United States Patent
Nolan et al.

(10) Patent No.: US 11,649,958 B2
(45) Date of Patent: May 16, 2023

(54) HIGH OUTPUT UV STERILIZATION MODULE WITH ENVIRONMENTAL FEEDBACK AND STERILIZATION OPTIMIZATION

(71) Applicant: M3 Innovation, LLC, Syracuse, NY (US)

(72) Inventors: Christopher D. Nolan, Camillus, NY (US); Joseph R. Casper, Baldwinsville, NY (US)

(73) Assignee: M3 Innovation, LLG, Syracuse, NY (US)

(*) Notice: Subject to any disclaimer, the term of this patent is extended or adjusted under 35 U.S.C. 154(b) by 178 days.

(21) Appl. No.: 17/032,077

(22) Filed: Sep. 25, 2020

(65) Prior Publication Data

US 2021/0154345 A1     May 27, 2021

Related U.S. Application Data

(60) Provisional application No. 62/940,644, filed on Nov. 26, 2019.

(51) Int. Cl.
*A61L 2/10* (2006.01)
*A61L 2/24* (2006.01)
(Continued)

(52) U.S. Cl.
CPC ............... *F21V 29/76* (2015.01); *A61L 2/10* (2013.01); *A61L 2/24* (2013.01); *A61L 2/26* (2013.01); *A61L 9/20* (2013.01); *F21S 2/00* (2013.01); *F21S 2/005* (2013.01); *F21S 4/28* (2016.01); *F21S 8/043* (2013.01); *F21S 8/085* (2013.01); *F21S 8/086* (2013.01); *F21V 21/002* (2013.01); *F21V 21/14* (2013.01); *F21V 21/30* (2013.01); *F21V 23/003* (2013.01); *F21V 23/008* (2013.01); *F21V 23/0435* (2013.01); *F21V 29/74* (2015.01); *H01R 24/84* (2013.01); *H05B 45/10* (2020.01); *H05B 45/37* (2020.01); *H05B 45/42* (2020.01); *H05B 45/44* (2020.01); *H05B 47/155* (2020.01); *H05B 47/165* (2020.01); *H05B 47/19* (2020.01); *H05B 47/20* (2020.01); *A61L 2202/11* (2013.01); *A61L 2202/14* (2013.01); *A61L 2202/25* (2013.01);
(Continued)

(58) Field of Classification Search
CPC . F21V 29/76; F21V 29/74; F21S 4/28; H05B 47/20; H05B 47/19; H05B 45/37; H05B 47/155; H05B 47/165; A61L 2/10; A61L 2/24; A61L 2/20; A61L 2/26
USPC .......................... 250/453.11, 454.11, 455.11
See application file for complete search history.

(56) References Cited

U.S. PATENT DOCUMENTS

| | | | |
|---|---|---|---|
| 2012/0126134 A1* | 5/2012 | Deal | G01J 1/429 250/372 |
| 2021/0299318 A1* | 9/2021 | Mullen | A61K 39/12 |

* cited by examiner

Primary Examiner — Nicole M Ippolito
(74) Attorney, Agent, or Firm — Aleksandar Nikolic

(57) ABSTRACT

An elongated lighting module having an asymmetric illumination source formed from at least two rows of light emitting diodes (LEDs) that extend along the long axis of the module and are independently controllable. The illumination source is rectangular and oriented so that the rows of LEDs extend along the long axis of the module. The module has couplings at each end that allow additional modules to be interconnected therewith using a linking member and a clamp. The lighting modules are powered via a wiring harness that extends down a support pole to a power converter stack having LED drivers to control the modules.

6 Claims, 26 Drawing Sheets

(51) Int. Cl.
*A61L 2/26* (2006.01)
*F21V 29/76* (2015.01)
*F21S 8/08* (2006.01)
*F21V 23/00* (2015.01)
*F21V 23/04* (2006.01)
*H05B 47/20* (2020.01)
*H05B 45/42* (2020.01)
*H05B 45/44* (2020.01)
*H05B 47/19* (2020.01)
*H05B 47/165* (2020.01)
*F21S 4/28* (2016.01)
*F21S 2/00* (2016.01)
*F21S 8/04* (2006.01)
*F21V 21/002* (2006.01)
*F21V 21/14* (2006.01)
*H01R 24/84* (2011.01)
*F21V 29/74* (2015.01)
*H05B 45/37* (2020.01)
*H05B 45/10* (2020.01)
*H05B 47/155* (2020.01)
*F21V 21/30* (2006.01)
*A61L 9/20* (2006.01)
*F21Y 105/16* (2016.01)
*F21Y 115/10* (2016.01)
*F21W 131/105* (2006.01)

(52) U.S. Cl.
CPC ........ *A61L 2209/11* (2013.01); *A61L 2209/12* (2013.01); *F21W 2131/105* (2013.01); *F21Y 2105/16* (2016.08); *F21Y 2115/10* (2016.08)

HIGH OUTPUT UV STERILIZATION MODULE WITH ENVIRONMENTAL FEEDBACK AND STERILIZATION OPTIMIZATION

CROSS-REFERENCE TO RELATED APPLICATIONS

The present application claims priority to U.S. Provisional Application No. 62/940,644, filed on Nov. 26, 2019, hereby incorporated by reference in its entirety.

BACKGROUND OF THE INVENTION

1. Field of the Invention

The present invention relates to sports lighting systems and, more specifically, to a lighting module that can provide ultraviolet (UV) sterilization employing asymmetric illumination sources.

2. Description of the Related Art

Mass gathering locations can present significant health risks such as those associated with viral outbreaks and pandemics. Indoor and outdoor sports venues can be particular troublesome as they position large numbers of people in close proximity and are difficult to disinfect between events. For example, conventional disinfection and/or sterilization requires manual cleaning of all surfaces in a stadium with harsh chemicals in order to adequate reduce the risk of spreading of a pathogen. This presents many problems, including the resources needed to perform the manual work, the difficulty in ensuring that all surfaces have been cleaned, and the time needed to perform the cleaning. In addition, some surfaces such as synthetic turf or elevated structures are extremely difficult to clean manually. Accordingly, there is a need in the art for an approach that can more easily assist with the disinfection and sterilization of sports venue to ensure the safety of spectators, staff, and players.

BRIEF SUMMARY OF THE INVENTION

The present invention is lighting system having a rectangular luminaire with an asymmetric lighting scheme that includes at least one series of LEDs that output energy in the ultraviolet (UV) spectrum along with or in lieu of white light for sterilization of the air and surfaces falling within the field of view of the luminaire. More specifically, the lighting system comprises a luminaire having a housing extending along a longitudinal axis and having an elongated opening and an illumination source positioned in the elongated opening of the housing of the luminaire and having at least two independently controllable rows of light emitting diodes that extend along the longitudinal axis. At least one of the independently controllable rows of light emitting diodes comprises light emitting diodes that emit illumination having wavelengths in the ultraviolet spectrum. The light emitting diodes that emit illumination having wavelengths in the ultraviolet spectrum may emit light with wavelengths between 100 to 290 nanometers. The light emitting diodes that emit illumination having wavelengths in the ultraviolet spectrum may emit light having a peak wavelength between 250 to 280 nanometers.

A controller may be interconnected to the illumination source that is programmed to control when the light emitting diodes that emit illumination having wavelengths in the ultraviolet spectrum are illuminated. The controller may be interconnected to a detector that provides data regarding environmental conditions proximate to the illumination source. The controller may be interconnected to a detector that provides data regarding occupancy of a location proximate to the illumination source. The controller may include a pathogen load calculator than can determine a pathogen load for at least a portion of the location proximate to the illumination source. The controller may include an illumination planner than can determine an illumination plan describing how the illumination source must be driven to provide sufficient illumination to disinfect the portion of the location proximate to the illumination source according to the pathogen load. The controller may be programmed to cause illumination of the illumination source according to the determination by the illumination planner of how the illumination source must be driven to provide illumination adequate to disinfect the portion of the location proximate to the illumination source.

The system may comprise a plurality of luminaires, each of which includes an illumination source having at least one independently controllable row of light emitting diodes that emits illumination having wavelengths in the ultraviolet spectrum. The illumination planner of the controller may be programmed to determine a plurality of illumination plans, each of which corresponds to one of the plurality of luminaires. The controller may be positioned in a remote host that is in wireless communication with each of the plurality of luminaires.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
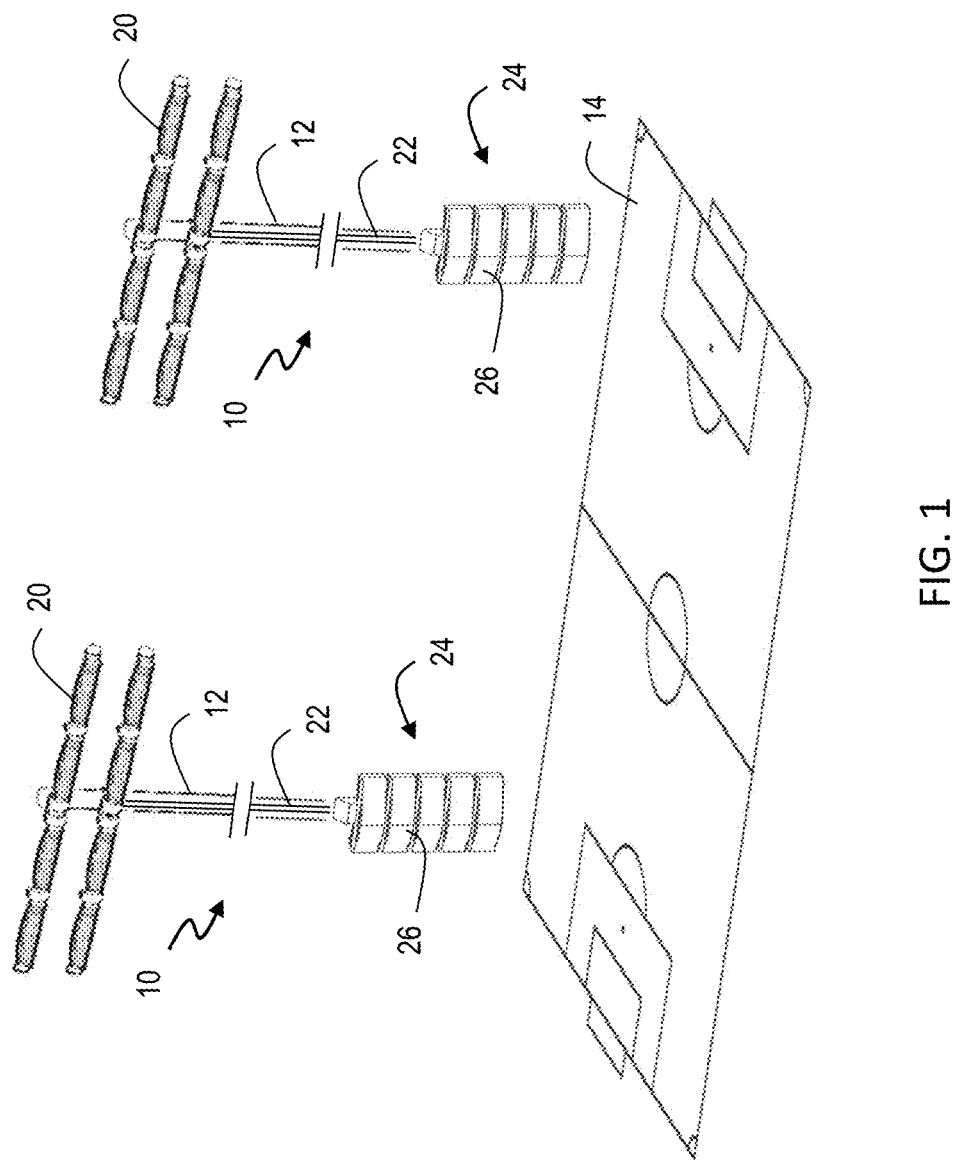
FIG. 1 is a perspective view of an asymmetric source sports lighting system according to the present invention.

Referring to the figures, wherein like numeral refer to like parts throughout, there is seen in FIG. 1 an asymmetric source sports lighting system 10 according to the present invention. System 10 is designed for installation on a support pole 12 to provide illumination over a target area 14, such as a sporting field or pitch. System includes one or more rows of light emitting diode (LED) lighting modules 20 that extend laterally from support pole 12. Lighting modules 20 are powered via a wiring harness 22 that extends along the interior of support pole 12 and is coupled to a controller stack 24. Controller stack 24 transforms local building power from AC to DC and includes LED drivers 26 for lighting modules 20.

Figure 2:
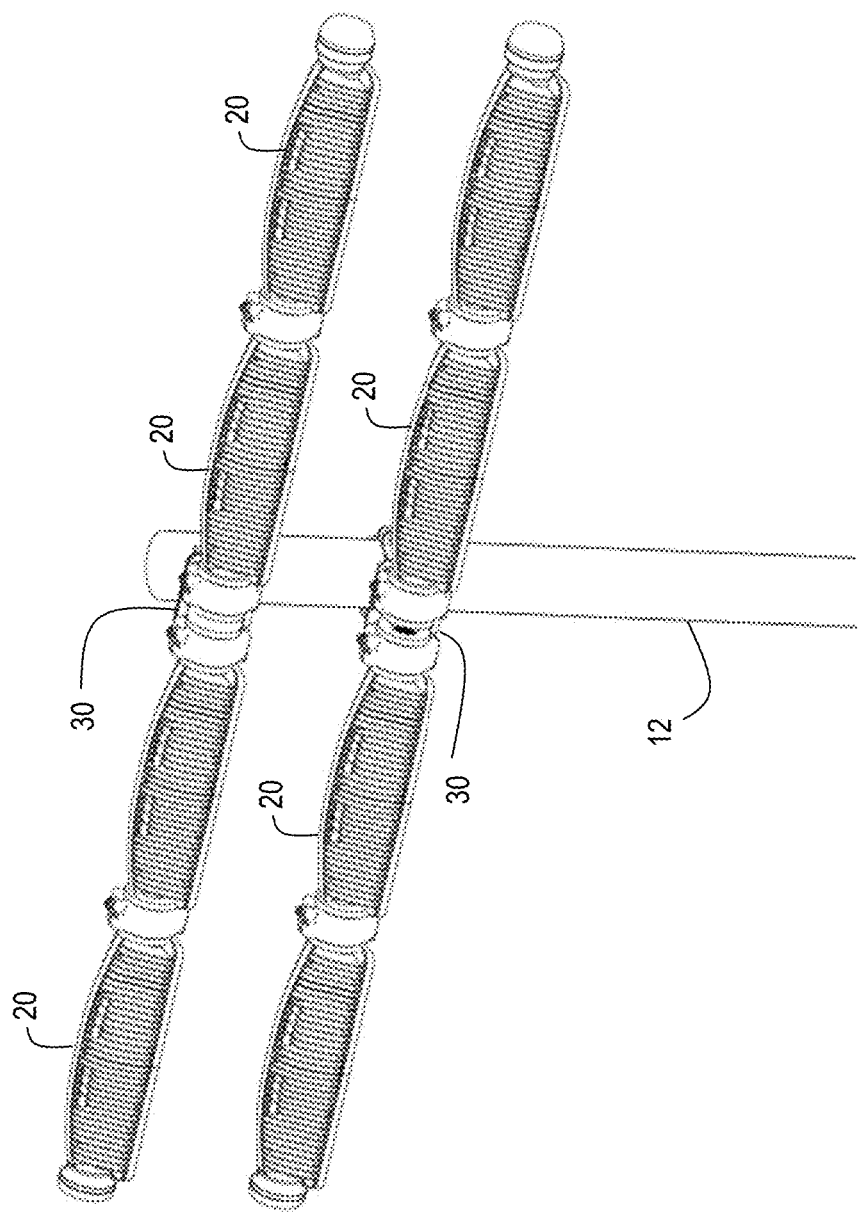
FIG. 2 is a perspective view of the upper portion of a support pole of an asymmetric source sports lighting system according to the present invention.

Referring to FIG. 2, a central mount 30 is coupled to pole 12 and used to support first and second lighting modules 20. Lighting modules 20 are coupled to either side of mount 30 using a modular coupling system described herein that physically supports modules 20 and electronically interconnects modules 20 to wiring harness 22 and thus controller stack 24. The opposing end of each lighting module 20 coupled to mount 30 may be used to physically support and electronically interconnect to additional lighting modules 20 extending further outwardly from support pole 12. The combination of lighting modules 20 connected to mount 30 and the additional lighting modules 20 extending to either side of pole 12 are self-supporting so that support pole 12 does not need to include physical cross-arms or lateral supports to mount additional lighting modules 20. The particular dimensions of lighting module 20 may be varied as desired. For example, lighting module 20 could be provided in two lengths, X and 2X, that may be mixed and matches as needed for a particular installation.

Figure 3:
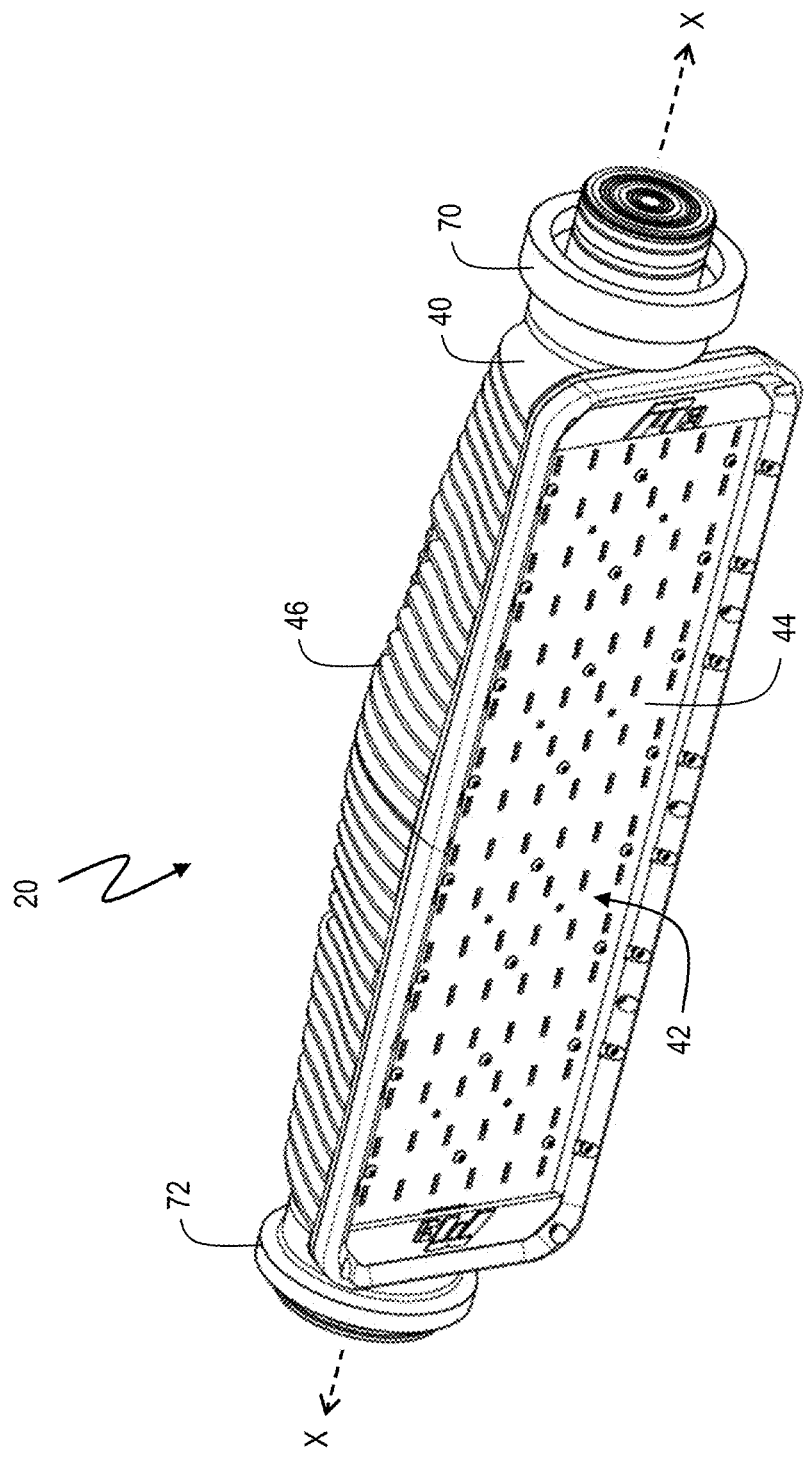
FIG. 3 is a perspective view of the asymmetric lighting source for a lighting module according to the present invention.

Referring to FIG. 3, each lighting module 20 includes a housing 40 extending along a longitudinal axis X-X. Housing 40 defines a rectangular opening 42 in a central portion thereof that permits access to an asymmetric illumination source 44. Asymmetric illumination source 44 is dimensioned to produce an asymmetric beam of illumination from rectangular opening 42 of module 20. Housing 40 may further include fins 46 or other external structures for dispersing heat generated by the use of asymmetric illumination source 44.

Figure 4:
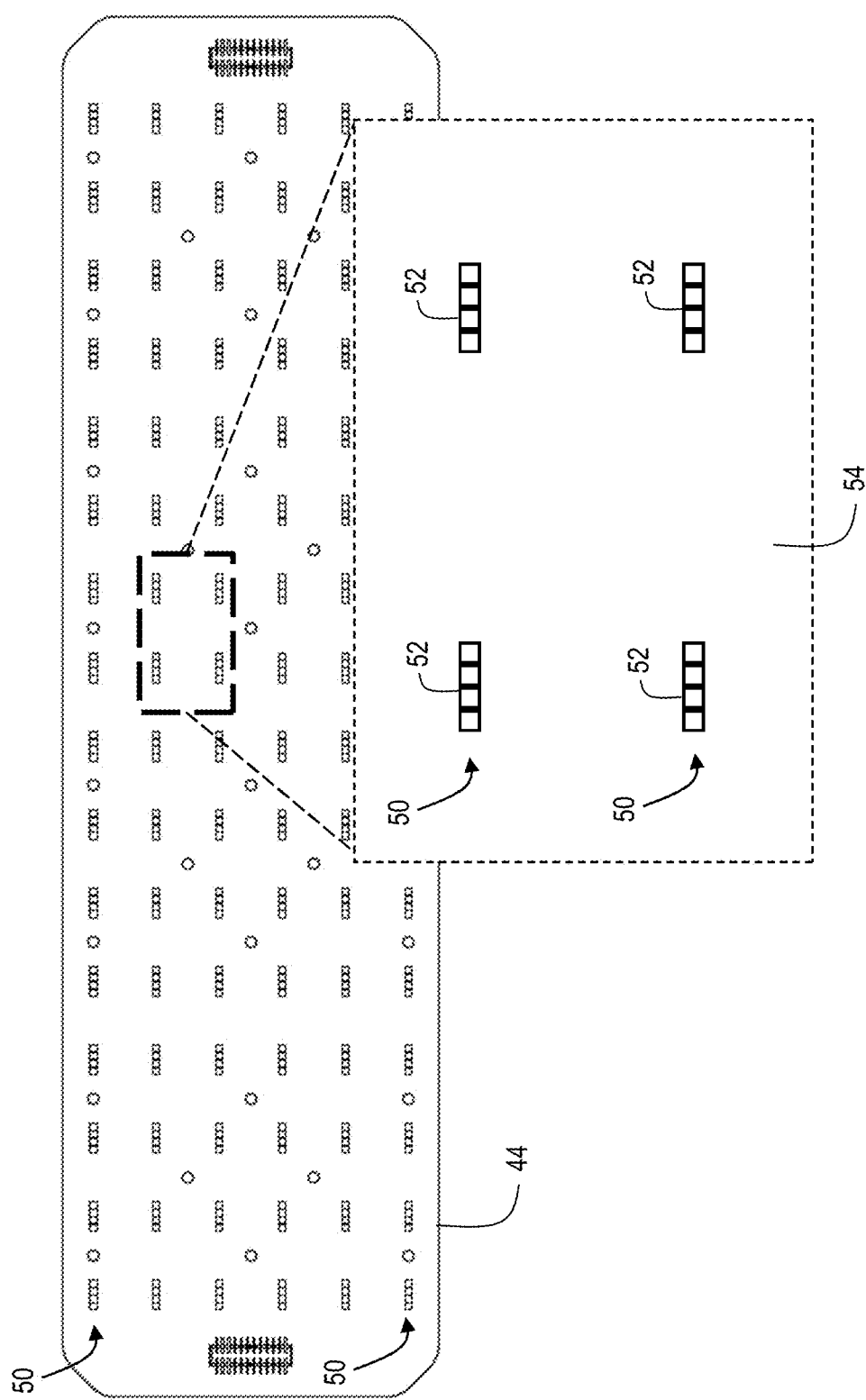
FIG. 4 is a mechanical view of the light emitting diode (LED) layout for an asymmetric lighting source according to the present invention.
Figure 5:
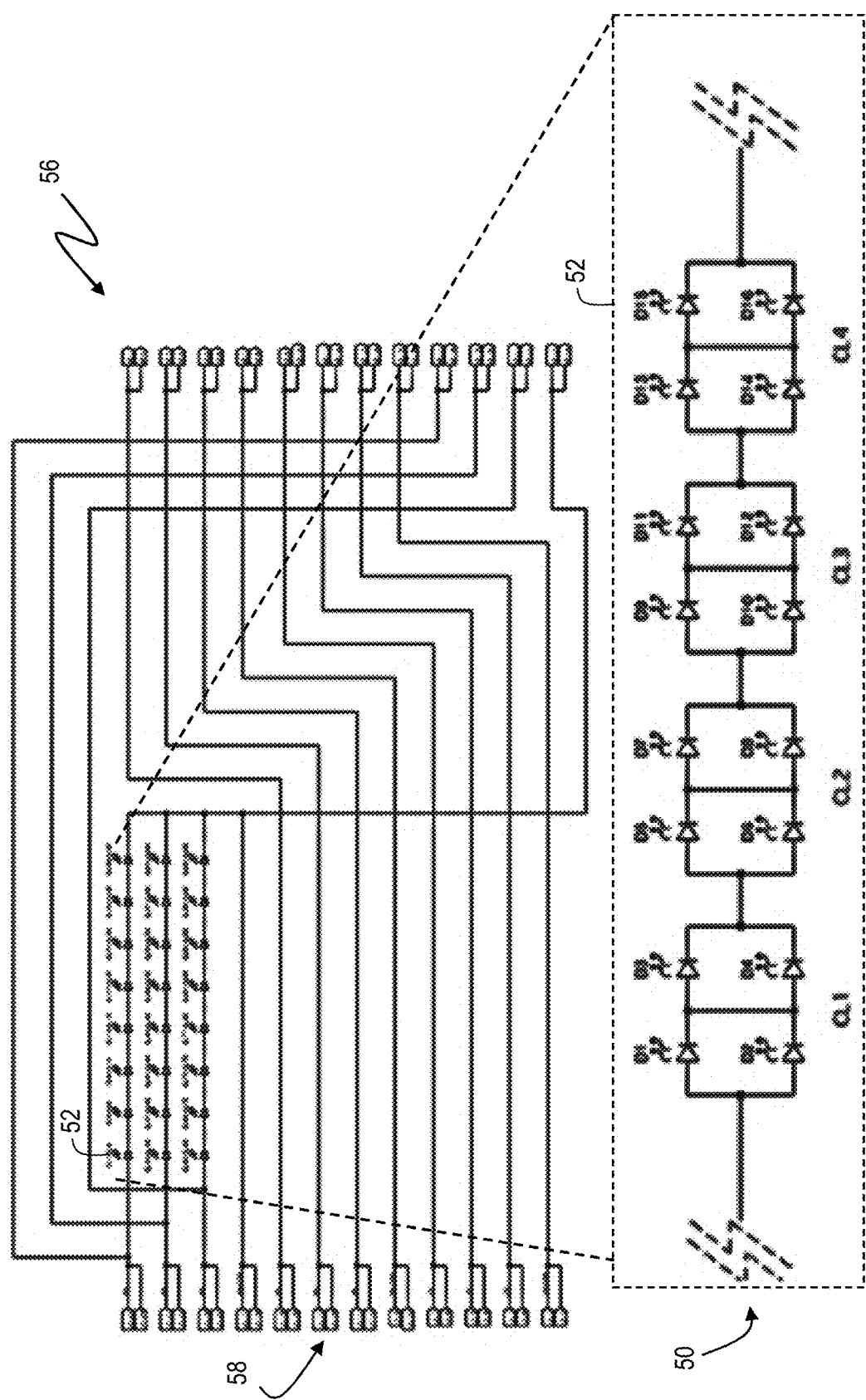
FIG. 5 is schematic of the electronics for an asymmetric lighting source according to the present invention.

Referring to FIGS. 4 and 5, asymmetric illumination source 44 comprises multiple rows 50 of light emitting diode (LED) sets 52 spaced along a substrate 54 and coupled to electronic circuitry 56 for asymmetrically driving illumination source 44. Each row 50, or optionally, each pair of rows 50, are independently controllable by adjusting the amount of power delivered to that row (or pair or rows) using electronic circuitry 56 and controller stack 24 to provide asymmetric illumination from module 20. Optionally, a local microcontroller in each module 20 can be for further adjustment of the amount of power provided to each row (or pair or rows) of LED sets 52. As seen in FIG. 5, asymmetric illumination source 44 having three independently controllable rows 50 of LED sets 52. Electronic circuitry 56 further includes pass-through circuitry 58 for providing power to adjacently connected lighting modules 20 that also include independently controlled rows 50 of LED sets 52. In the example of FIG. 5, a total of two additional lighting modules 20 may be interconnected and supported by circuitry 58.

LED sets 52 may comprise any combination of wavelength LEDs, including those that emit, or are filtered to emit, UVA wavelengths (320 to 400 nanometers), UVB wavelengths (290 to 320 nm), and UVC wavelengths (100 to 290 nm). UVC wavelengths are generally regarding as the best wavelength range for germicidal effects, with peak effects between 250 to 280 nm, and thus would be preferred when asymmetric illumination source 44 is to be used for disinfecting or sterilizing purposes in a location. For example, optimal bacterial disinfection occurs with a UVC peak of 265 to 267 nm. As described above, asymmetric illumination source 44 may have multiple rows 50 of LED sets 52, and thus may be configured to have all visible light wavelength LED sets 52, all UV wavelength LED sets 52, or any combination thereof depending on the total number of rows 50. Acceptable UV emitting LEDs are available commercially, although the particular wavelength and power output from the particular LEDs selected for system 10 may need to be confirmed to ensure the appropriate delivery of the desired UV dosage for disinfection or sterilization as described herein.

The specific positioning of the UV wavelength LED sets 52 can provide for precise control over the application of UV light in a location. The amount of UV radiation needed for disinfection at a given wavelength is referred to as the UV dose (millijoules per centimeter squared) and is the product of the UV intensity (milliwatts per centimeter squared) and the exposure time (second). The desired UV dose in location 14, such as that needed to achieve at least a 6 Log reduction to be called disinfection, may be achieved by dividing the UV dose required for the 6 Log reduction by the UV intensity available in a given location to determine how long the UV illumination must be provided to that location achieve disinfection. Differences in UV intensity between different areas within location 14 may thus require asymmetric illumination sources 44 being driven for different lengths of time if the user prefers to avoid operating all illumination sources 44 according to the amount of time needed for the area requiring the longest period of illumination. For example, a particular area of location 14 may be associated with multiple asymmetric illumination sources 44 having at least one UV LED set 52, while other area may only have a single asymmetric illumination source 44 with an UV LED set 52 directed therein, thereby having a lower UV intensity.

Figure 6:
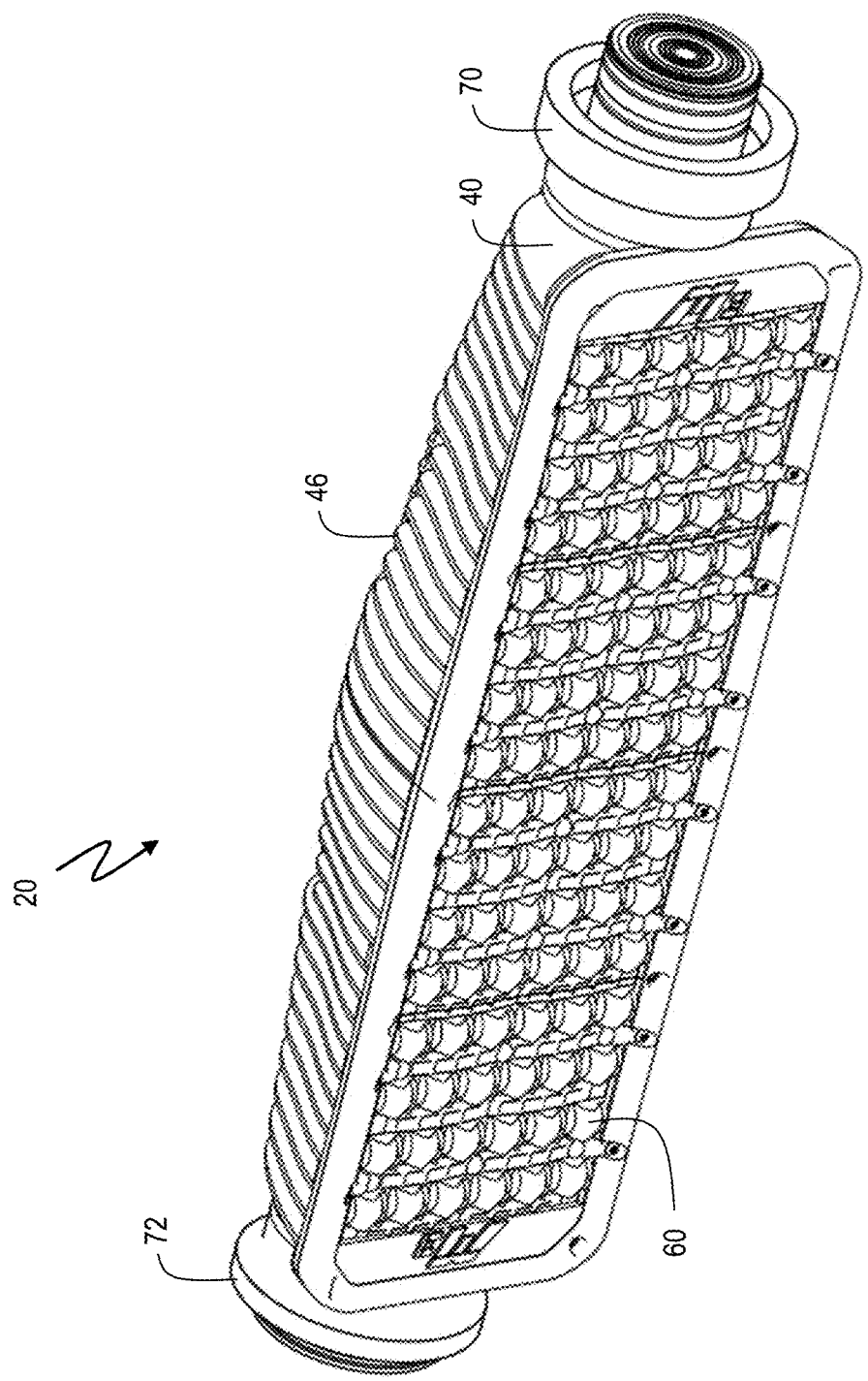
FIG. 6 is a perspective view of a lighting module according to the present invention having a lens array thereon.

Referring to FIG. 6, a molded lens array 60 is positioned over an asymmetric illumination source 44 to reduce harshness and provide sealing of asymmetric illumination source 44 within housing 40. Housing 40 of module 20 is further configured to allow for easy coupling to the support pole and to other housings 40, forming both structural and electrical connection. Housing 40 includes a male coupler 70 positioned at one end of housing 40 and a female coupler 72 positioned at an opposing end of housing 40. Male coupler 70 is defined by a a radially extending flange 74 and a circumferentially extending, outwardly facing bearing surface 76. Female coupler 72 includes a correspondingly dimensioned flange 78 and a receptacle 82 defining a circumferentially extending, inwardly facing bearing surface 77.

Figure 7:
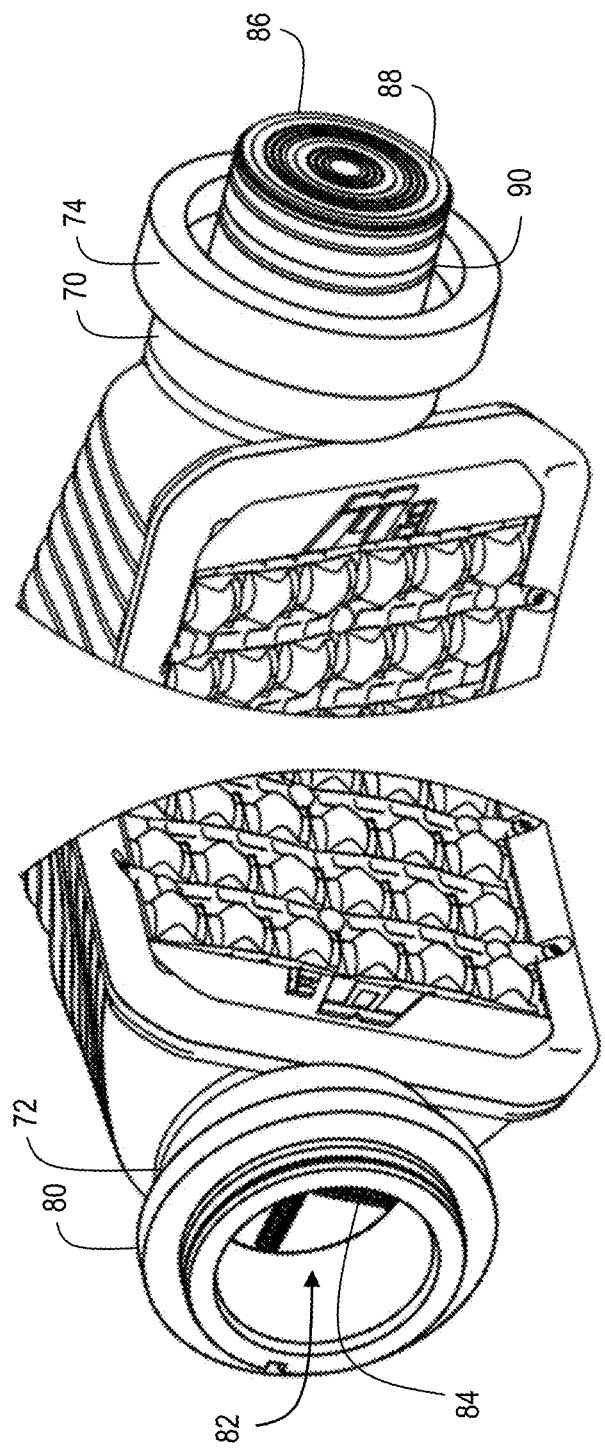
FIG. 7 is a perspective view of the male and female couplers of a lighting module according to the present invention.
Figure 8:
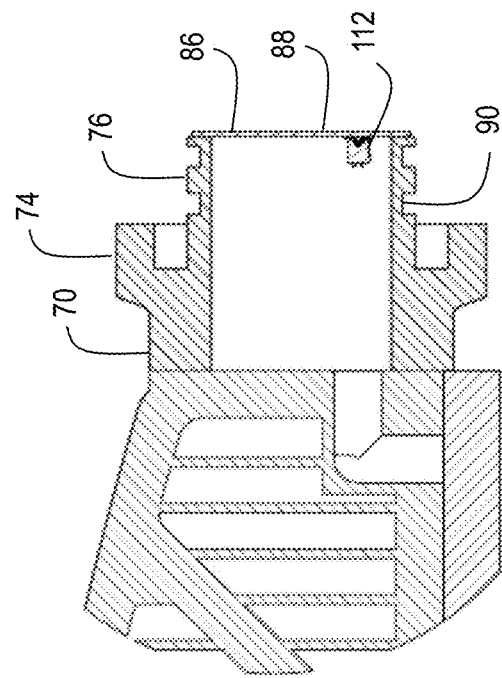
FIG. 8 is a cross-sectional view of the male and female couplers of a lighting module according to the present invention.
Figure 8:
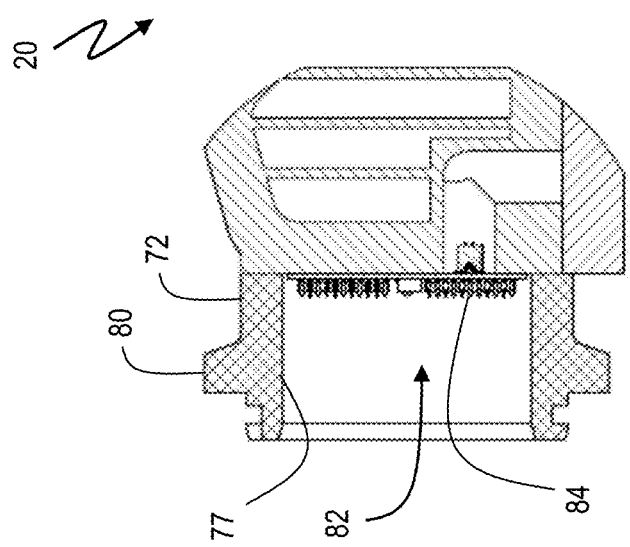

Referring to FIGS. 7 and 8, female coupler 72 further includes a set of brush contacts 84 positioned in receptacle 82 that face outwardly along axis X-X and male coupler 70 includes an end face 86 supporting set of ring contacts 88 that face outwardly in the opposite direction along axis X-X from brush contacts 84. Male coupler 70 may additionally include grooves 90 formed therein to house an O-ring for sealing purposes. It should be recognized that other contacts may be used, such as pogo pins and the like. As detailed below, brush contacts 84 and ring contacts 88 define a plurality of independent pathways for powering the independently controlled rows 50 of LED sets 52.

Figure 9:
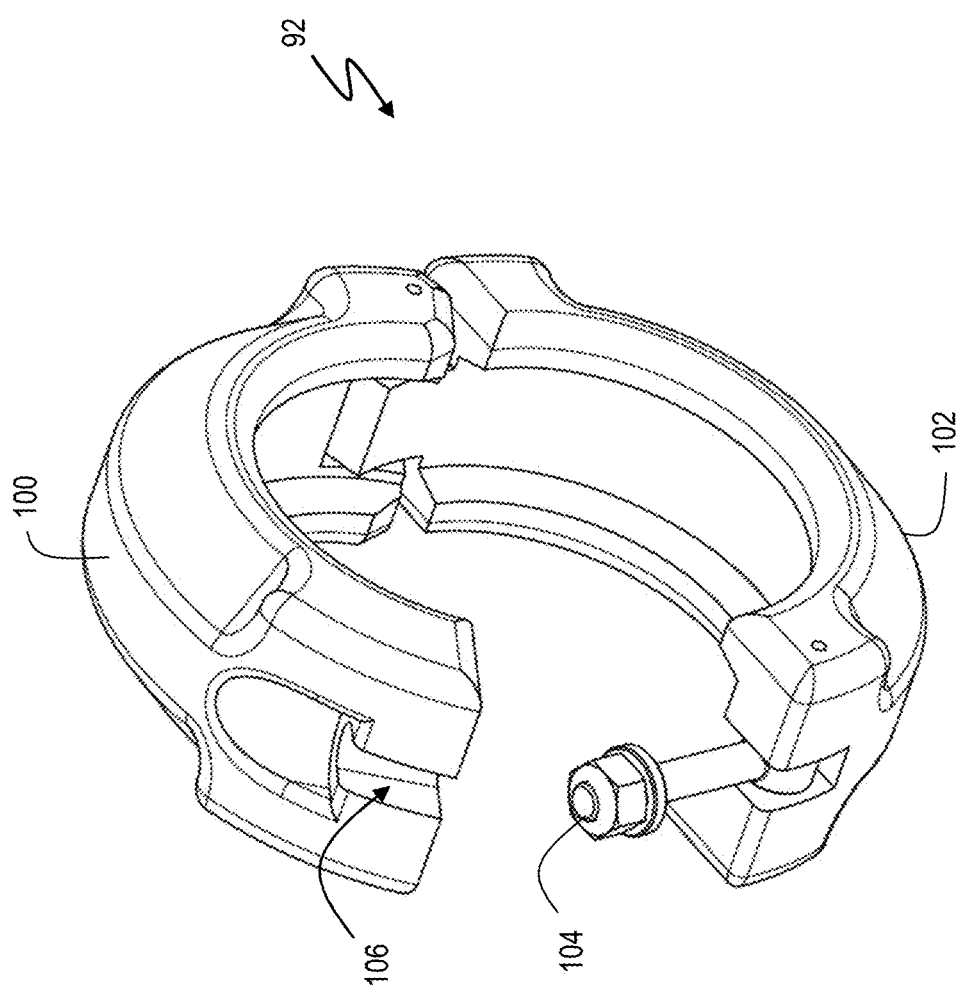
FIG. 9 is a perspective view of a coupler clamp for securing lighting modules to each other according to the present invention
Figure 10:
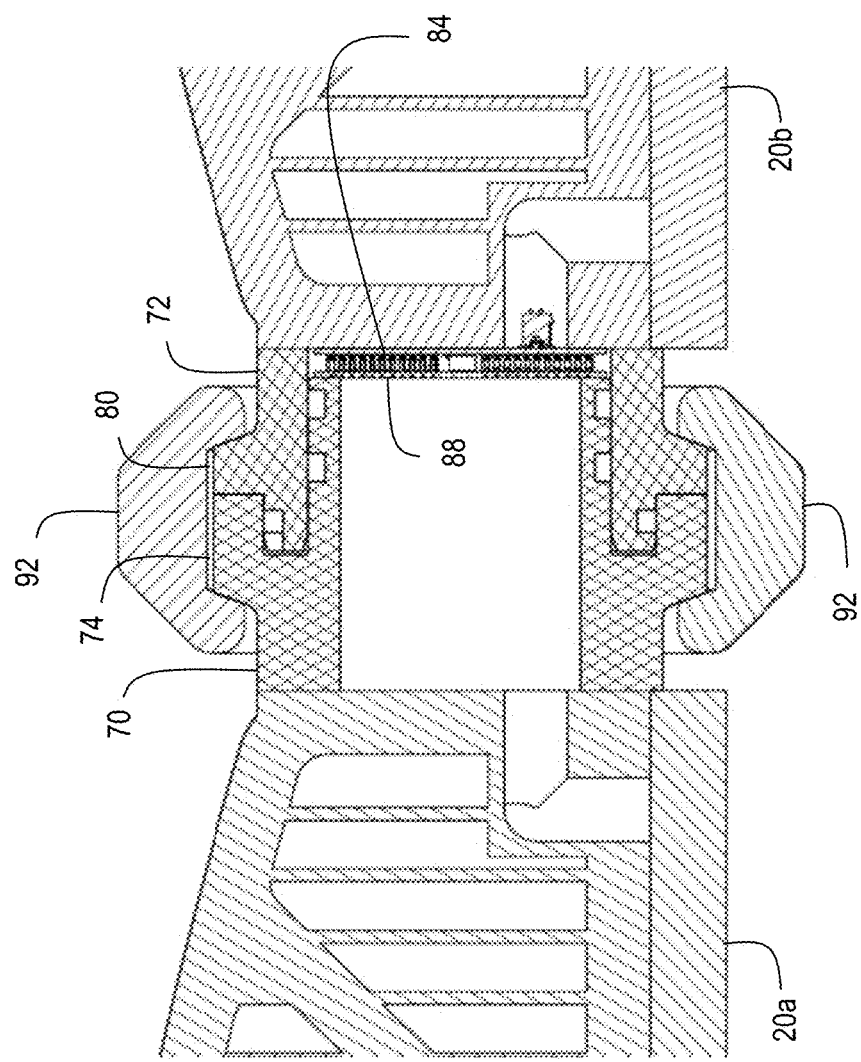
FIG. 10 is cross-sectional view of a lighting module to lighting module connection according to the present invention.

Referring to FIGS. 9 and 10, a clamp 92 may be positioned and secured in covering relation to flanges 74 and 80 to secure a first module 20a to a second module 20b when male coupler 70 and female coupler 72 are full joined so that bearing surfaces 76 and 77 are in seated together and brush contacts 84 and ring contacts 88 are in contact and electrically engaged. Clamp 92 comprises a pair of jaws 100 and 102 that can be opened and then closed in covering relation to flanges 74 and 80, as seen in FIG. 10, when male coupler 70 of one module 20a is jointed with and seated inside female coupler 72 of an adjacent module 20b. When male coupler 70 is fully inserted into female coupler 72, flanges 74 and 80 will abut and brush contacts 84 will physically and electrically engage ring contacts 88. Clamp 92 may then be closed over flanges 74 and 80 to secure first module 20a to second module 20b using a latch 104 on one jaw 102 that cooperates with a slot 106 in the other jaw 100, with electrical continuity between first module 20a to second module 20b provided via the engagement of ring contacts 88 with brush contacts 84. Adjacent modules 20 may thus be electrically interconnected when coupled together so that each module 20 has multiple independent electrical power pathways for driving the independently controllable LED rows of asymmetric illumination source 44.

Figure 11:
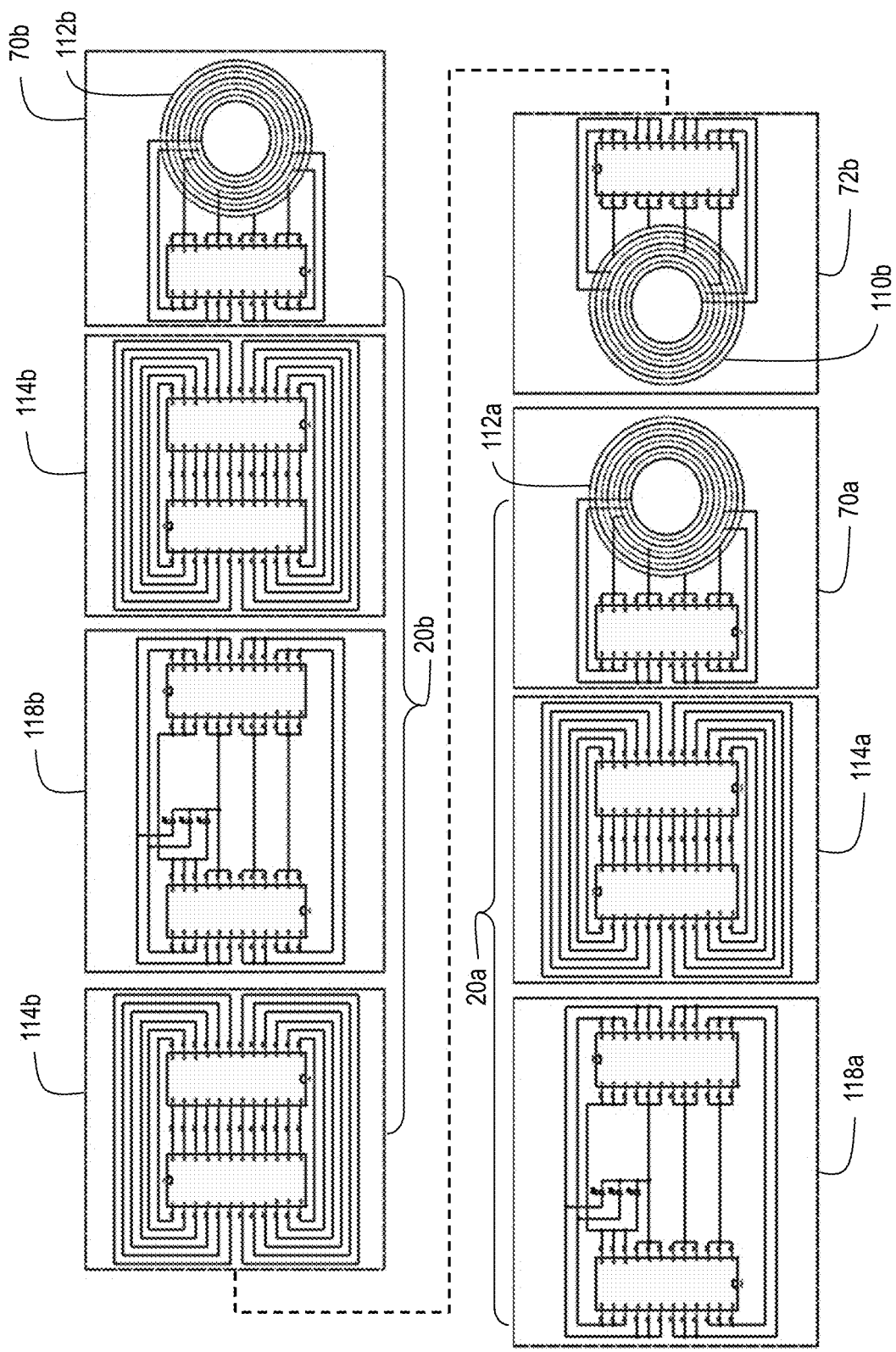
FIG. 11 is an electrical diagram of a lighting module to lighting module connection according to the present invention.

Referring to FIG. 11, module 20b is electrically interconnected to module 20a so that LED circuitry 118b of module 20b and LED circuitry 118a of module 20a are coupled together and under common power control. For example, coupler 70b of module 20b includes coupler circuitry 112b that can receive power from ring contacts 88. Coupler circuitry 112b is coupled to LED circuitry 118b via cabling 114b. LED circuitry 118b is also coupled to coupler circuitry 110b associated with female coupler 72b via cabling 114b. As a result, independent power pathways for LED circuitry 118b extend through module 20b and are available at coupler 70b and coupler 72b such as that a power supply connected to coupler 70 will also provide power to coupler 72, and vice versa. As further seen in FIG. 11, module 20a can be electrically coupled to module 20b via a coupler 70a that is secured to coupler 72b. Coupler circuitry 112a of module 20a is coupled to LED circuitry 114a via cabling 114a. Although not illustrated for simplicity, it should be evident that module 20a also include a coupler 72a that can be, in turn, coupled to another module 20, and so on, with the power supply for all housings 20 connected to an available coupler 70 or 72 at either end. Thus, module 20 is bi-directional and can be placed in series with additional housings 20 for common power control.

Figure 12:
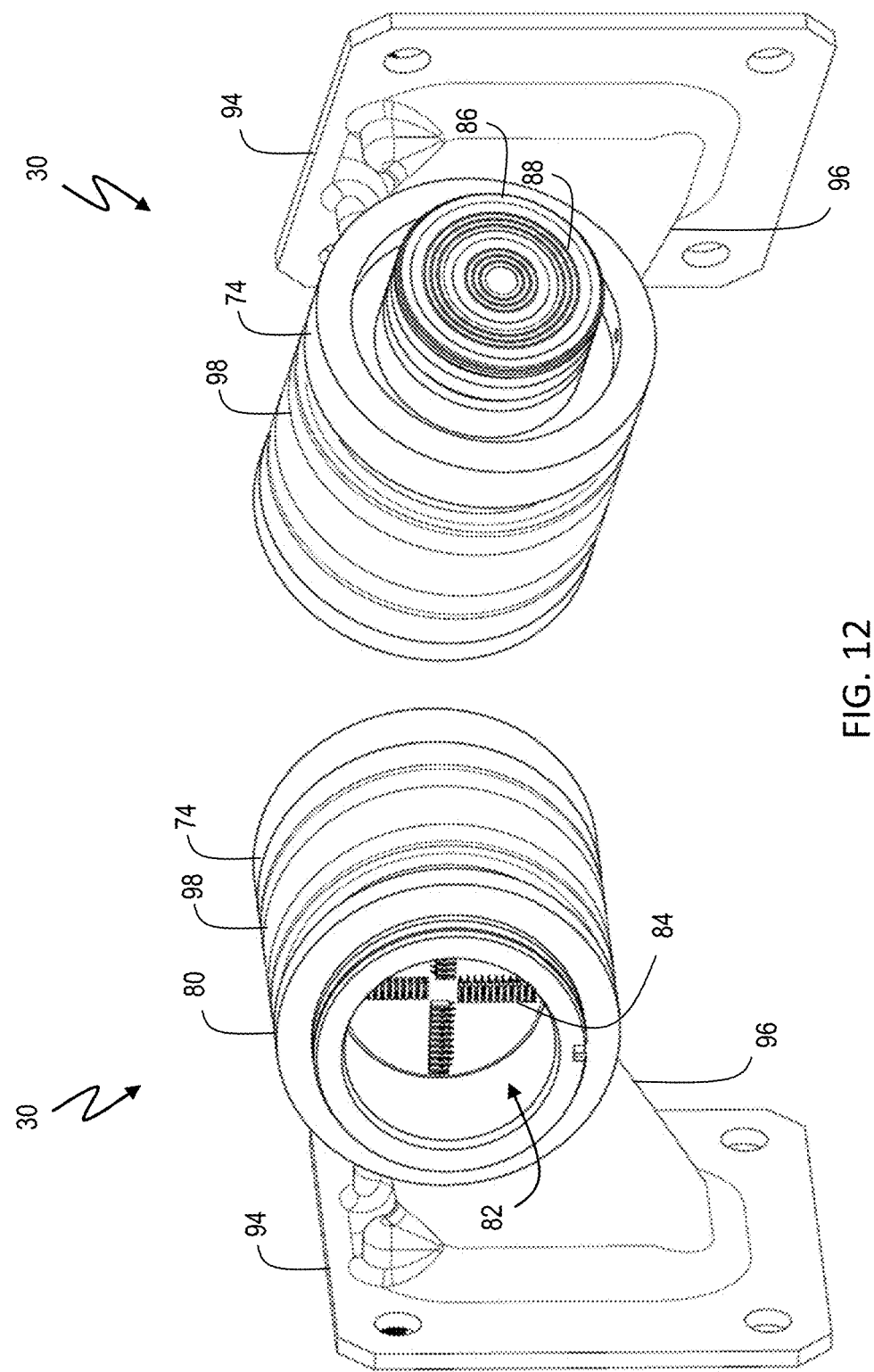
FIG. 12 is two perspective views of a mount according to the present invention.

Referring to FIG. 12, mount 30 for attaching one or more housings 20 to a support pole 12 comprises a mounting plate 94 having a shaft 96 extending therefrom to support a main body 98 having male coupler 70 on one side and a female coupler 72 on the opposing side. Mount 30 suspends module 20 in spaced relation to support pole 12 to which mount 30 is attached. Male coupler 70 and female coupler 72 are configured in same manner as described above with respect to module 20, i.e., male coupler 70 includes an end face 86 having concentric ring contacts 88 and female coupler 72 has brush contacts 84 positioned within receptacle 82. Male coupler further includes flange 74 and female coupler 72 includes flange 80. As a result, module 20 may be coupled to mount 30 in the same manner as described above with respect to the connection of module 20a to module 20b.

Figure 13:
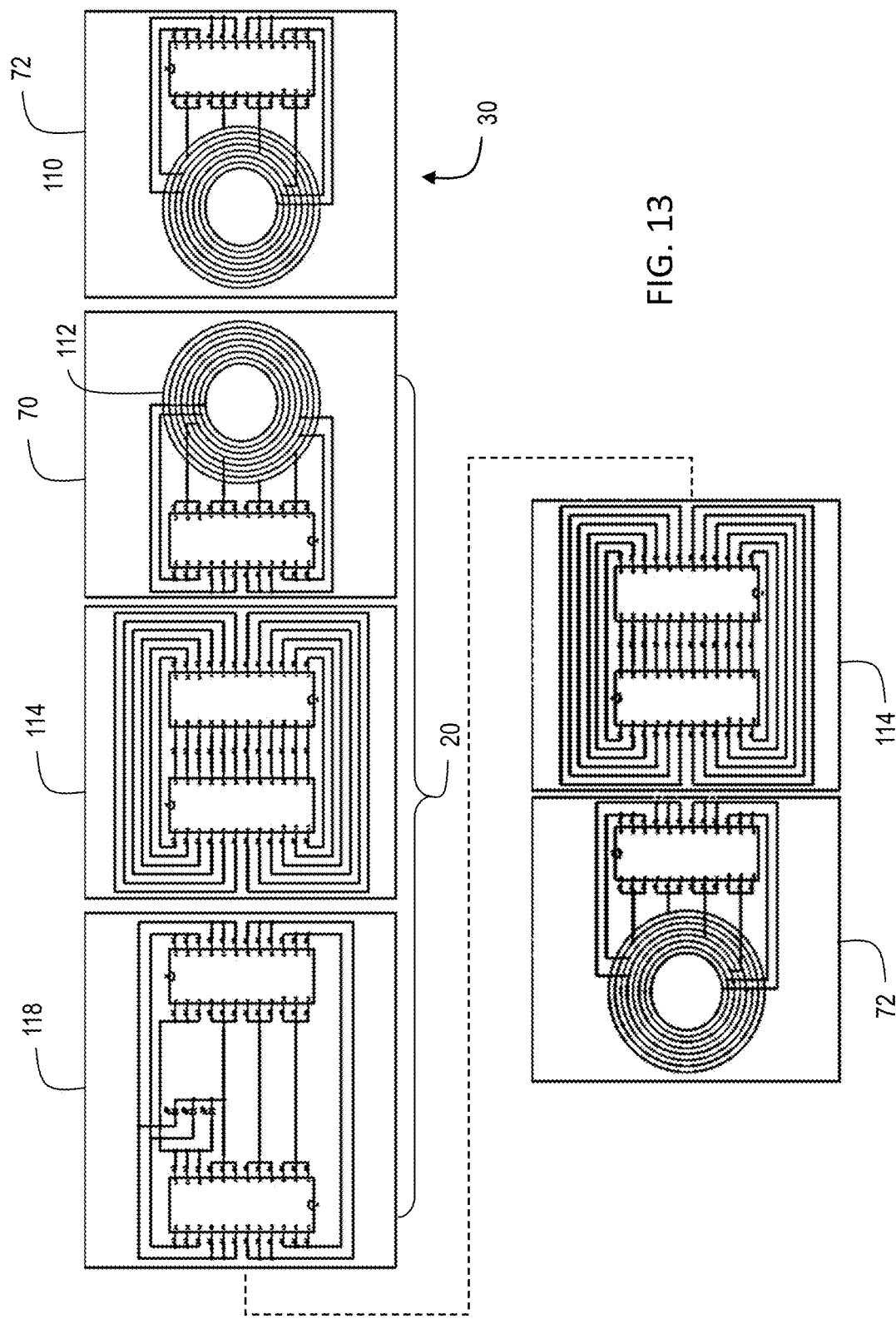
FIG. 13 is an electrical diagram of a lighting module to mount connection according to the present invention.

Referring to FIG. 13, joining of mount 30 to module 20 allows coupler circuitry 110 of female coupler 72 of mount 30 to connect with coupler circuitry 112 of male coupler 70 of module 20 via brush contacts 84 and ring contacts 88. Coupler circuitry 112 is coupled to LED circuitry 118 via cabling 114. LED circuitry 118 is also coupled to coupler circuitry 110 associated with female coupler 72 via cabling 114. As a result, independent power pathways for LED circuitry 118b extend through module 20 from mount 30 and are available at coupler 70 such that a power supply connected to coupler 72 will also provide power to coupler 70. Similarly, module 20 may also be connected to the male coupler 70 of mount 30 using female coupler 72 of module 20, thus simply reversing the connections of FIG. 13 such that power is provided by mount 30 to coupler 72 with the power also made available at coupler 70 for attachment of another module 20.

Figure 14:
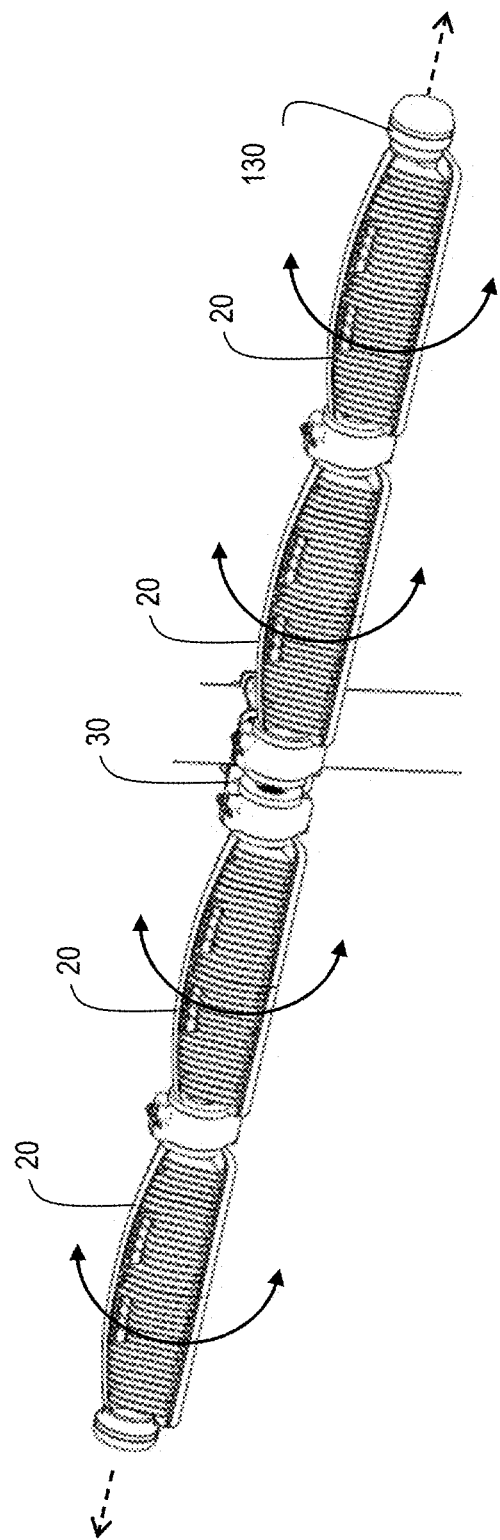
FIG. 14 is a perspective view showing axial rotation of a series of interconnected lighting modules according to the present invention.

Referring to FIG. 14, cylindrical bearing surfaces of male coupler 70 and female coupler 72 allows adjacent lighting modules 20, as well as lighting modules 20 coupled to mount 30, to be rotated about longitudinal axis X-X. The orientation of the rectangular illumination provided by module 20 may thus be adjusted in a single direction, i.e., about a single axis, via rotation of lighting module 20 about axis X-X. As explained above, bearing surfaces 76 and 77 allow for physical rotation of housings 20, with brush contacts 84 and ring contacts 88 maintaining electrical continuity regardless of the rotation of housing about longitudinal axis X-X. Housings 20 may thus be easily oriented, or reoriented, as desired. While housings 20 may be manually adjusted at any time, servo motors could be incorporated into couplers 70 and 72 to allow for remote rotation of lighting modules 20 about axis X-X.

Figure 15:
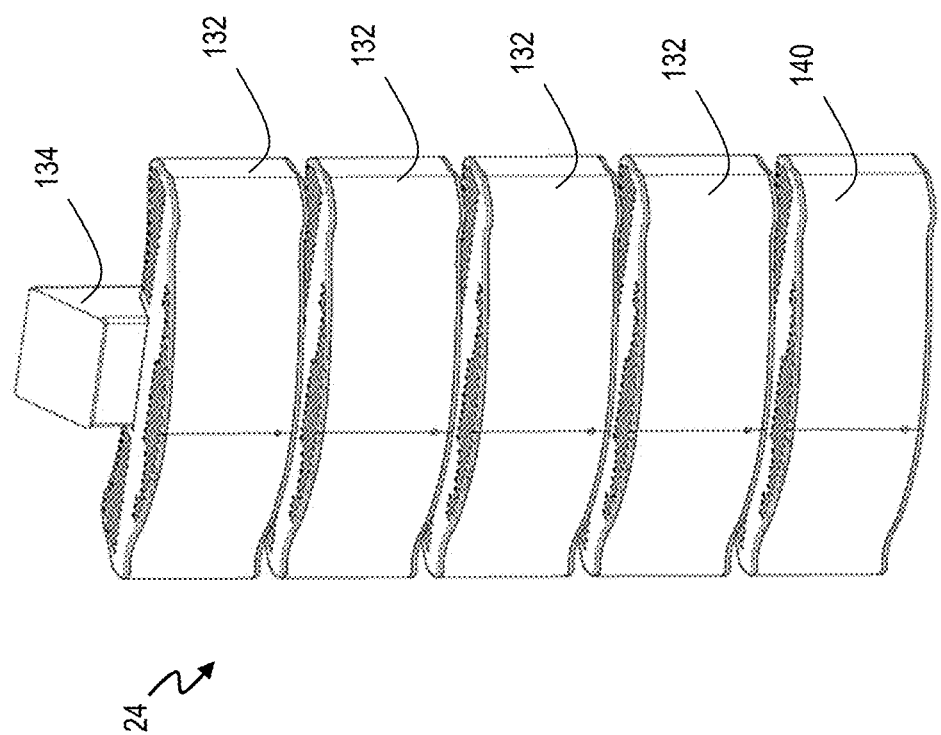
FIG. 15 is a perspective view of a controller stack according to the present invention.
Figure 16:
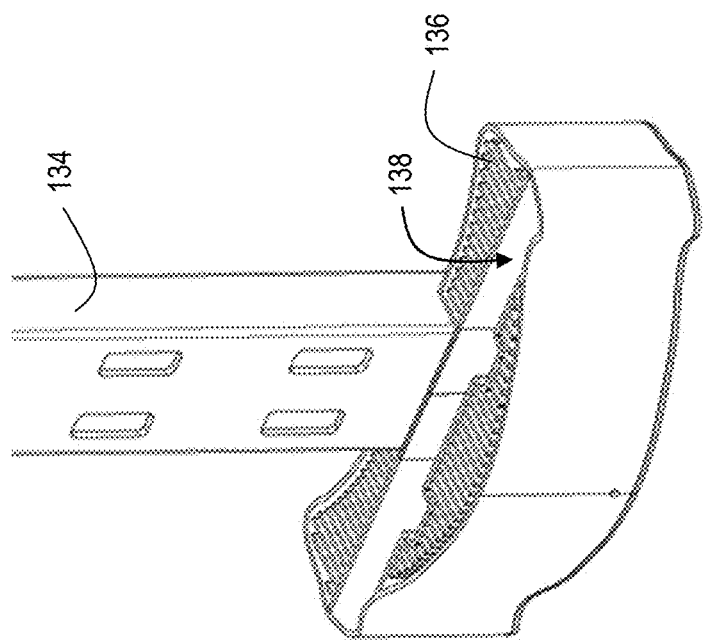
FIG. 16 is a perspective view of a core enclosure according to the present invention.

Referring to FIGS. 15 and 16, controller stack 24 comprises a series of core enclosures 132, each of which houses the power conversion and LED electronics, typically referred to as LED drivers, for an associated lighting module 20, as well as a master enclosure 140 that provides housekeeping functions. Controller stack 24 includes a back plane 134 that provides the electrical interconnections between each core enclosure 132 and master enclosure 140 as well as the requisite interconnections to wiring harness 22 to interconnect controller stack 24 to lighting modules 20. Back plane 134 is preferably adapted to act as a heat sink and transfer excess heat to support pole 12 for additional dispersion of heat generated by controller stack 24. As seen in FIG. 16, core enclosure 132 and/or master enclosure 140 include ribs 136 for dissipation of heat generated by internal electrical components positioned in a central cavity 138.

Figure 17:
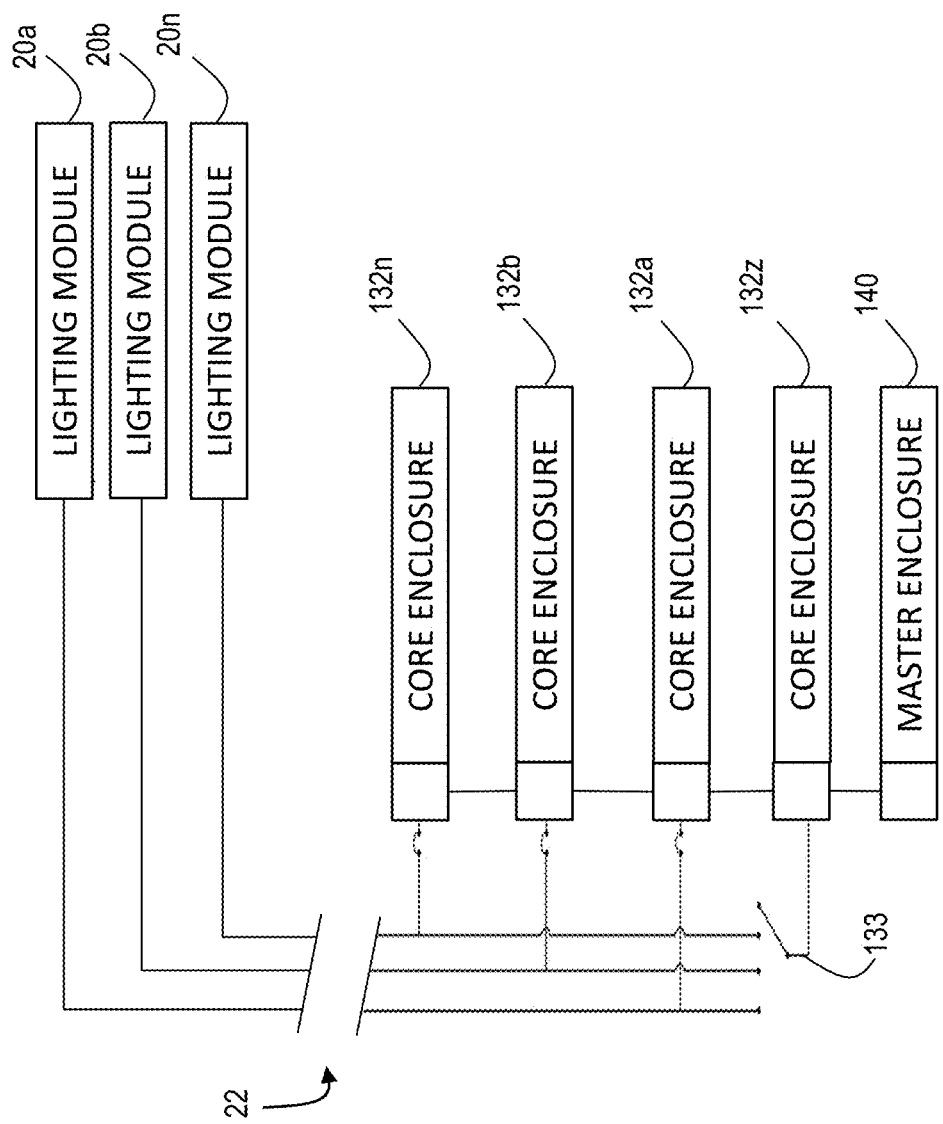
FIG. 17 is high level schematic for a lighting system according to the present invention.

Referring to FIG. 17, each core enclosure 132a, 132b . . . 132n is associated with and coupled via wiring harness 22 to a corresponding lighting module 20a, 20b . . . 20n. Preferable, a backup core enclosure 132z is selectively coupled to each lighting module 20a, 20b . . . 20n via a switching circuit 133 to provide a backup power supply in the event of a fault in any of core enclosure 132a, 132b . . . 132n. For example, if a fault in any core enclosure 132 results in the loss of illumination from any or all of the independently controlled rows 50 of LED sets 52 in the corresponding lighting module 20, power to that lighting module 20 can be switched to the backup core enclosure 132z to maintain the desired amount of illumination until such time as the faulty core enclosure 132 can be repaired or replaced. Each core enclosure 132a, 132b . . . 132n is also interconnected to master enclosure 140, which supervises and controls via digital commands the local operation of each core enclosure 132a, 132b . . . 132n.

Figure 18:
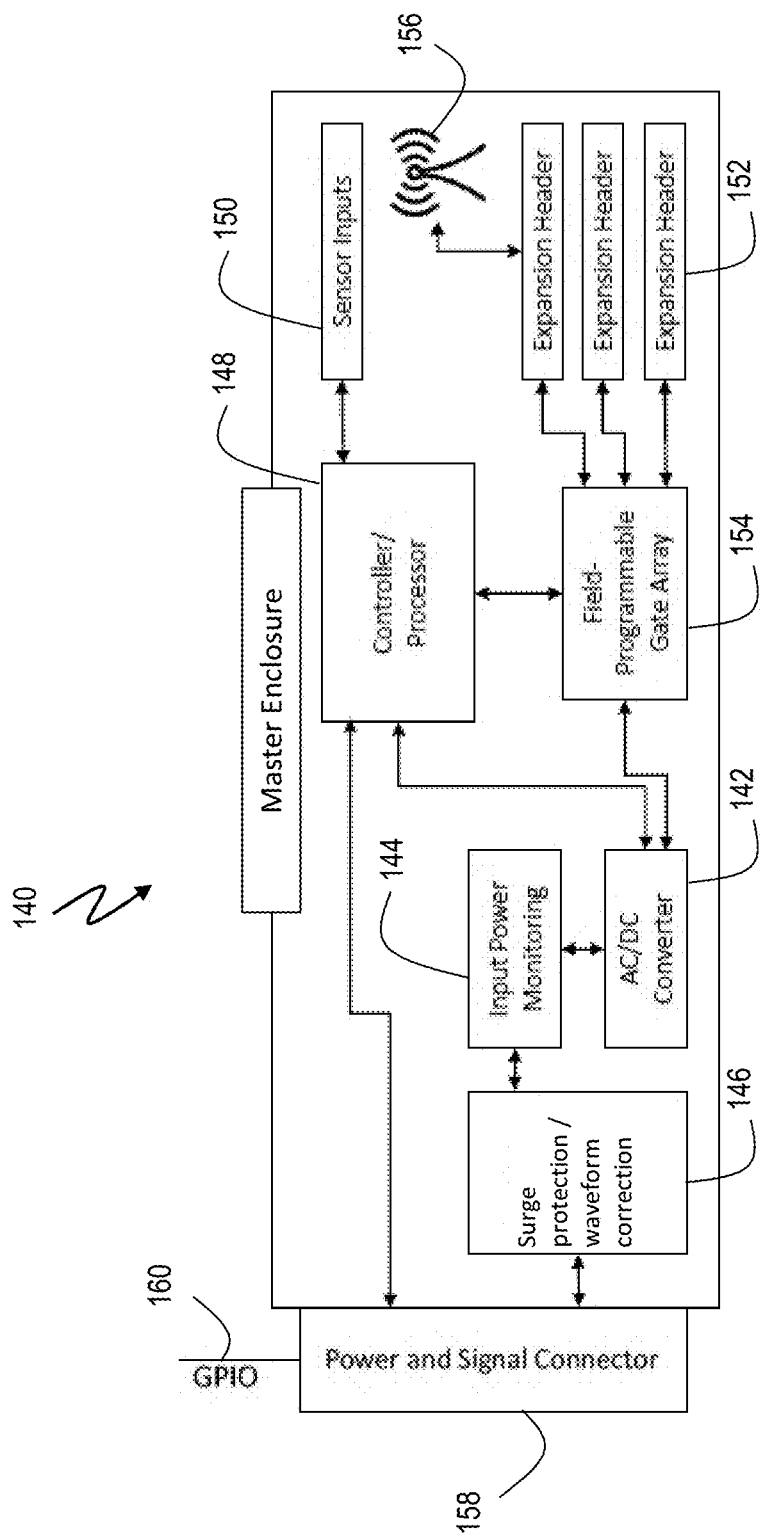
FIG. 18 is a detailed schematic of a master controller according to the present invention.

Referring to FIG. 18, master enclosure 140 is coupled to AC power via a power and signal connector 158 and includes local AC/DC conversion 142 with input power monitoring 144 as well as surge protection and waveform correction 146. Master enclosure 140 also includes a controller/processor 148 that has sensor inputs 150 for monitoring of system 10. Controller/processor 148 is also interconnected to a series of expansion headers 152 and wireless communication interface 156 via a field programmable gate array (FPGA) 154.

Controller/processor 148 may thus be programmed to establish connection with a remotely positioned host system or remote device (such as a tablet or smartphone) that can provide commands controlling operation of lighting modules 20 using expansion headers 152 to provide the desired wireless connectivity. Communication could comprise any conventional wireless communication technology or protocol, such as WiFi, Blutetooth®, BLE, ZigBee, Z-Wave, 6loWPAN, NFC, cellular such as 4G, 5G or LTE, RFID, LoRA, LoRaWAN, Sigfox, NB-IoT, or LIDAR. Controller/processor 148 is also coupled via power and signal connector 158 for communication with core enclosures 132, such as via a general-purpose input/output (GPIO) line 160, extending in back plane 134.

Figure 19:
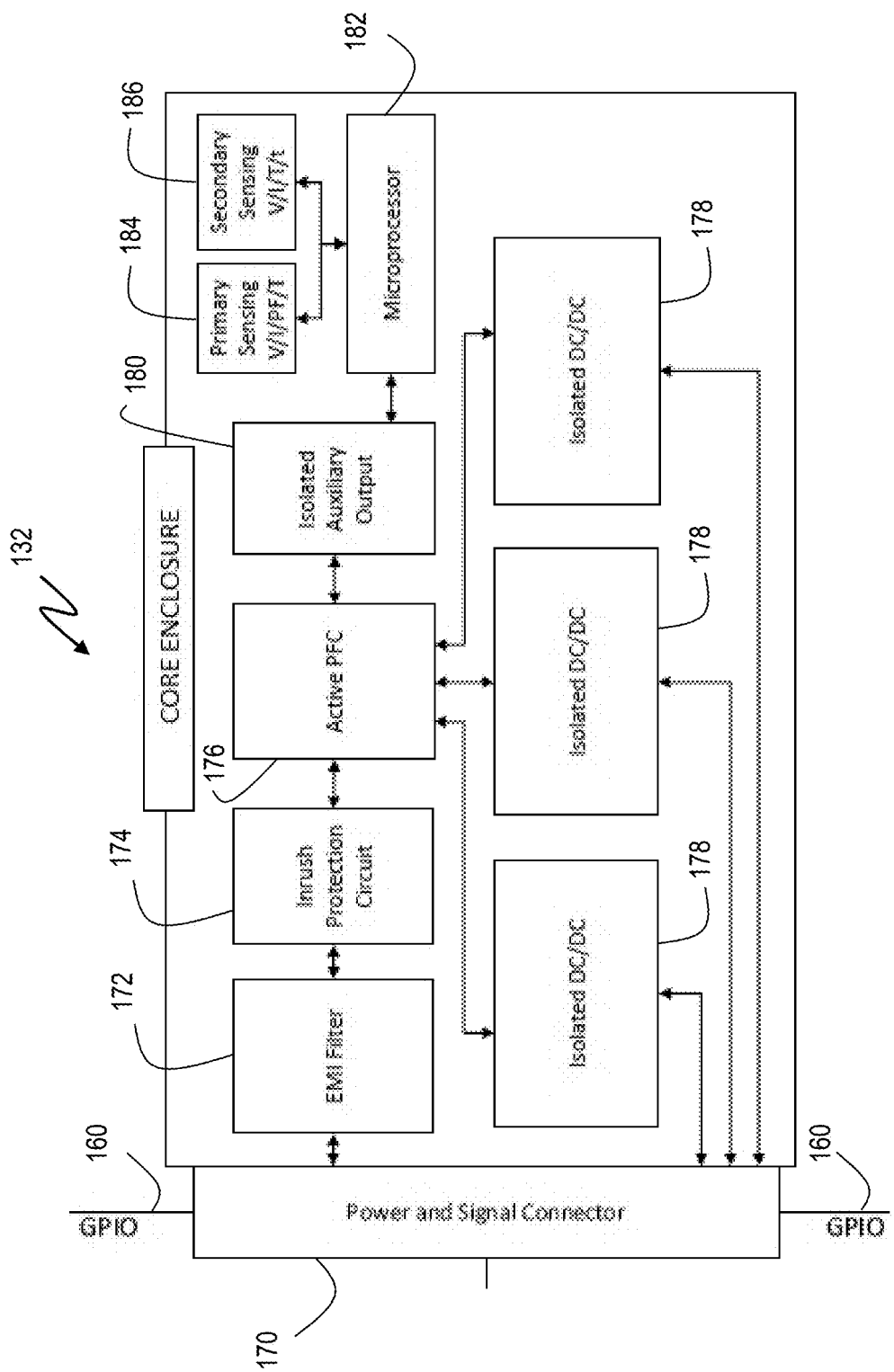
FIG. 19 is a detailed schematic of a core enclosure according to the present invention

Referring to FIG. 19, each core enclosure 132 includes a power and signal connector 170, which provides connectivity to master enclosure 140 via GPIO line 160 as well as to a connection to AC power. Core enclosure 132 provides power conversion to DC and power conditioning via an EMI filter 172, an inrush protection circuit 174 and an active power factor corrector (PFC) 176. A plurality of isolated DC/DC circuits 178, each of which supports a corresponding one of independently controllable LED rows of asymmetric illumination source 44, are coupled to active PFC 176. The present invention is illustrated with three isolated DC/DC circuits because the exemplary illumination source 44 has three independently powered rows of LEDs, but if asymmetric illumination source 44 included four independently controlled rows 50 of LED sets 52, four isolated DC/DC circuits 178 would be included. Core enclosure 132 further comprises an isolated auxiliary output 180 coupled to a microprocessor 182. Microprocessor 182 is further coupled to primary sensing circuits 184 and secondary sensing circuits 186 for monitoring voltage, current, power factor, and temperature across system 10. Microprocessor 182 is further configured to adjust the power output from each of the plurality of isolated DC/DC circuits 178 based on monitoring of primary sensing circuits 184 and secondary sensing circuits 186. For example, if one of independently controlled rows 50 of LED sets 52 is not operational, microprocessor 182 can adjust the power output from the isolated DC/DC circuits 178 for the other of the independently controlled rows 50 of LED sets 52 to compensate for the loss and ensure that asymmetric illumination source 44 is providing the desired amount of illumination.

Figure 20:
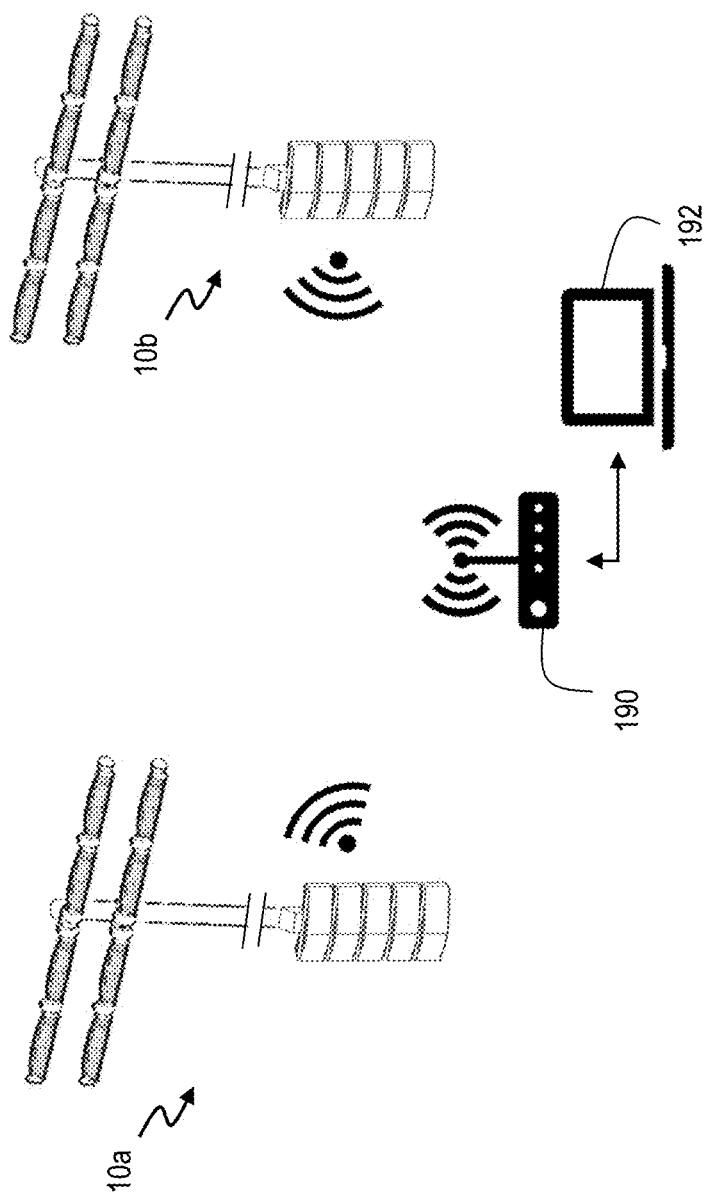
FIG. 20 is a schematic of wireless monitoring and control approach according to the present invention.

Referring to FIG. 20, the wireless communication capability of master enclosure 140 provides a third layer of redundancy in the event of a partial or total loss of illumination from lighting module 20. For example, a detected loss at one location of system 10a may be communicated to wireless gateway 190 and remote host 192. The illumination output of another system 10b may then be adjusted accordingly, either by allowing a user to send a command to system 10b to adjust power to lighting modules 20 to compensate for the detected loss or by supervisory software residing on host 192 that automatically sends the appropriate commands.

Figure 21:
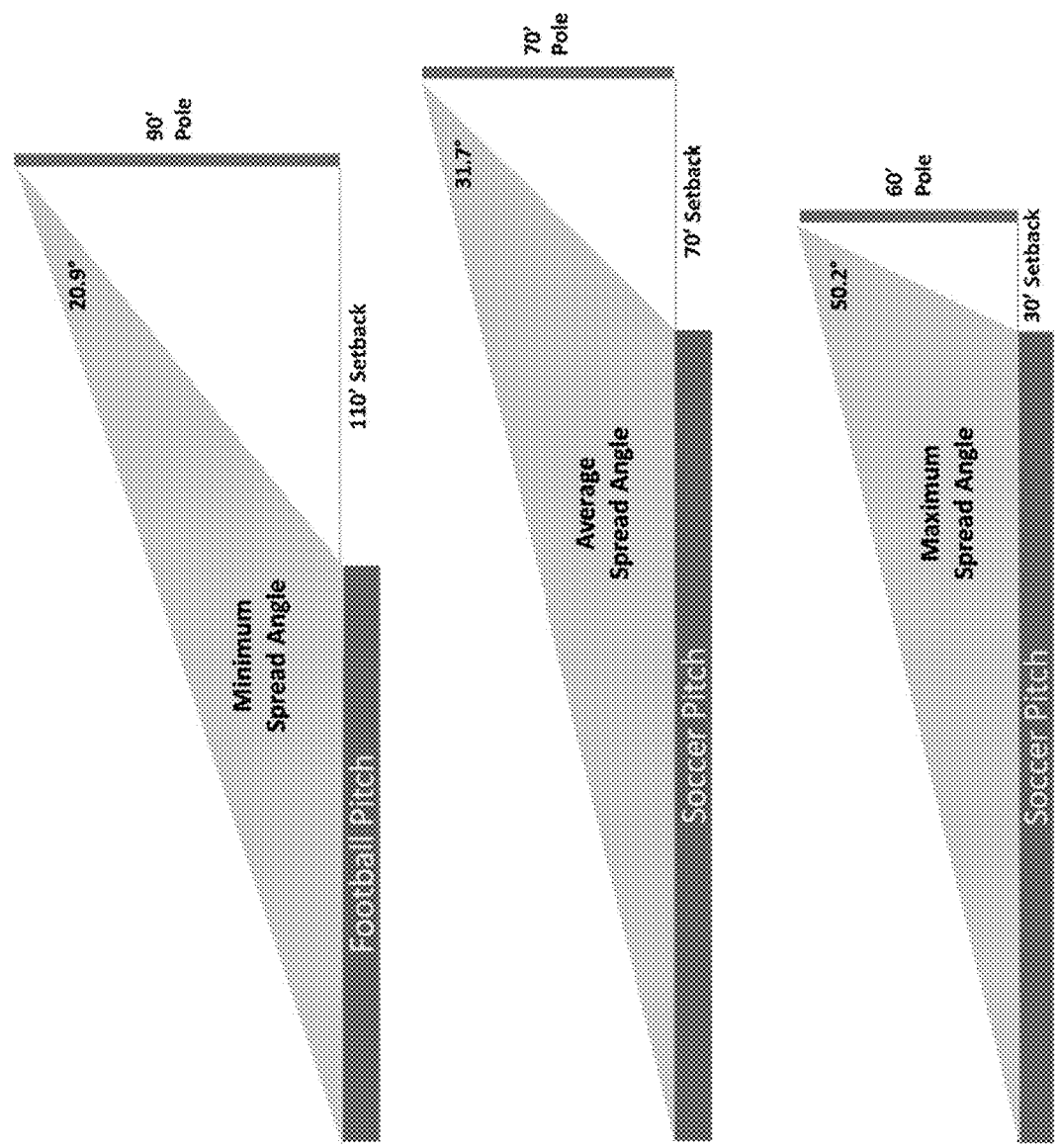
FIG. 21 is a schematic of beam steering using a lighting system according to the present invention.
Figure 22:
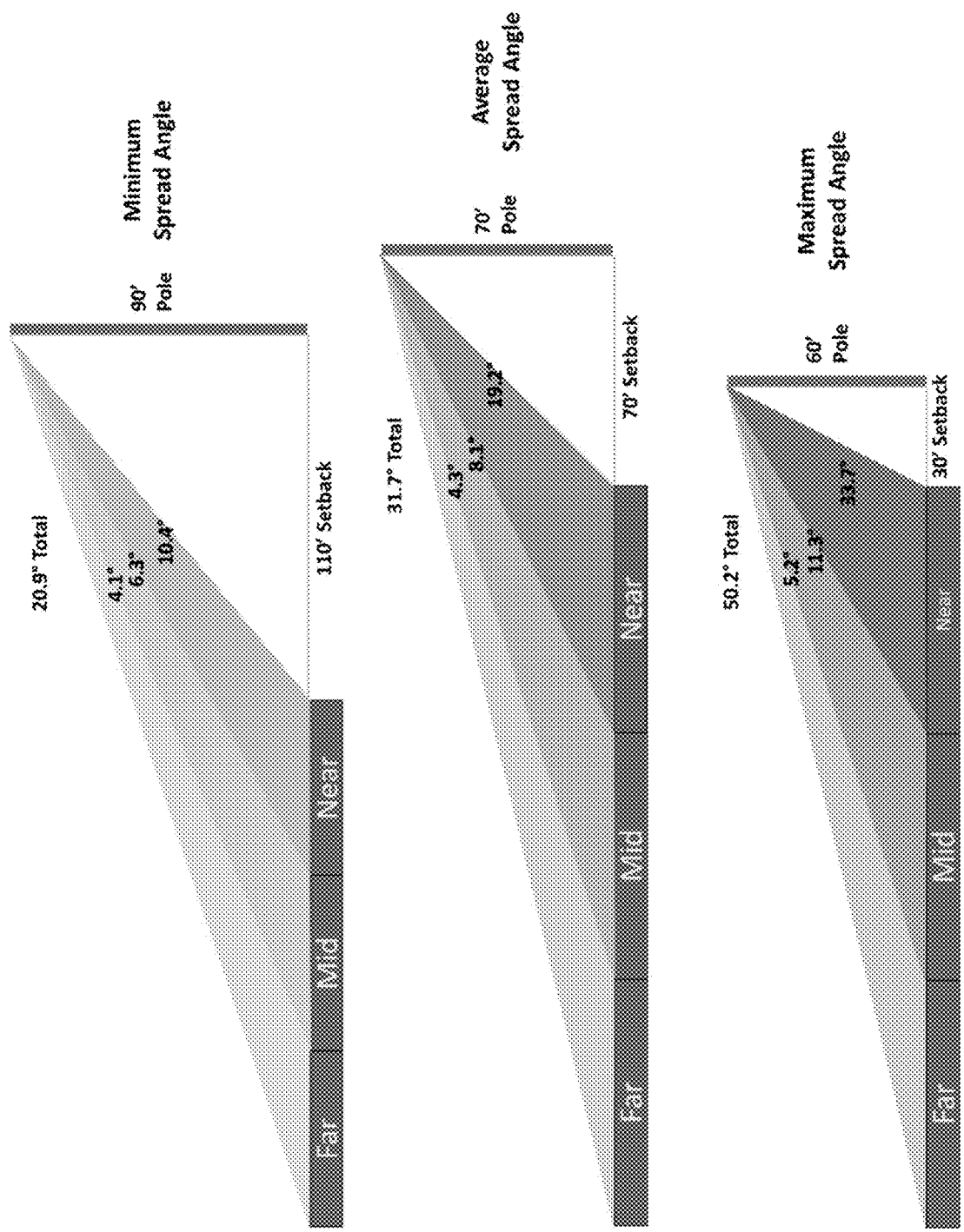
FIG. 22 is a schematic of beam angles changes using a lighting system according to the present invention.

Referring to FIG. 21, asymmetric illumination source 44 of each module 20 allows for remote beam steering of lighting system 10. Lighting system 10 may be adapted to a particular installation regarding of the width of the pitch to be illuminated, the height of support pole 12, and the distance between support pole 12 and the targeted pitch. For example, asymmetric illumination source 44 may be driven to change the beam angle (generally recognized as the region of illumination with at least fifty percent of the maximum beam strength) to provide the appropriate amount of illumination between a minimum and maximum spread angle encountered in an installation. In the first scenario of FIG. 21, where the height of support pole 12 and setback distance require a minimum spread angle, asymmetric illumination source 44 can be driven asymmetrically in a first configuration to provide a narrow beam angle without having to physically reorient modules 20. In the last scenario, where the height of pole 12 and setback distance require a minimum spread angle, asymmetric illumination source 44 can be driven asymmetrically in a different configuration to provide a broader spread angle without having to physically reorient modules 20. Thus, the effective positioning of modules 20 can be adjusted without actually having to physically reorient modules 20. Thus, modules 20 may be asymmetrically driven to change the illumination scenario for different events or conditions, or to simply adjust the illumination in a given location without having to physically move lighting modules 20. FIG. 22 illustrates how the power control over each row 50 of asymmetric illumination source 44 can be adjusted to impact the beam angle emitted from lighting module 20 without having to rotate lighting module 20.

Figure 23:
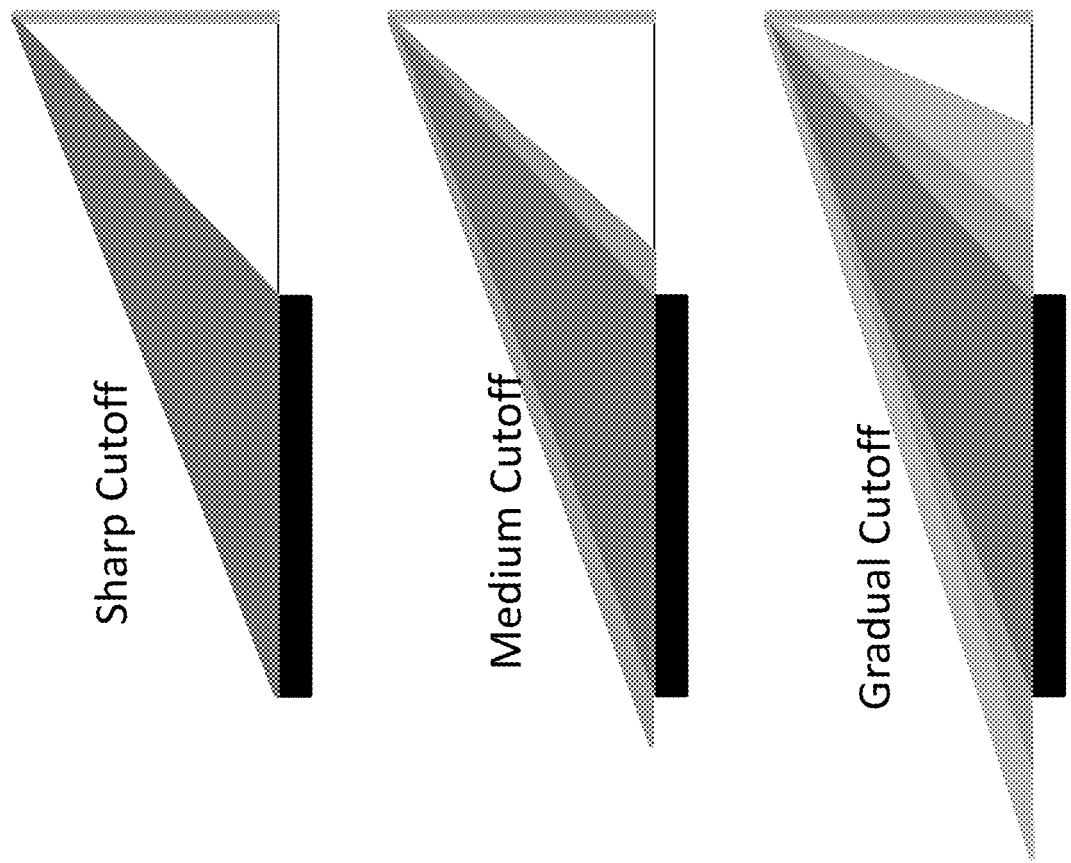
FIG. 23 is a schematic of tunable cut-off in a lighting system according to the present invention.

Referring to FIG. 23, asymmetric illumination source 44 of each lighting module 20 provides for a tunable cut-off for the illumination generated from lighting module 20. Illumination cut-off generally refers to the amount of illumination in the beam field that extends beyond the desired beam angle (any area of illumination with less than fifty percent but more than ten percent of the maximum beam strength). For example, in the first scenario of FIG. 23, the cut-off is very sharp, i.e., there is very little spillage beyond the main beam angle. In the second and third scenarios, the spillage increases such that more illumination is provided ancillary to the primary beam angle. Asymmetric illumination source 44 may be driven to change the cut-off at any time, whether finally upon installation, or dynamically over time to change the lighting scheme as desired by a user for different applications. For example, a gradual cut-off may be selected when more light is desired in the areas surrounding a pitch for a particular event, such as a pre-game show, and then adjusted to provide a sharp cut-off during a game. Thus, asymmetric illumination source 44 allows for control over both the beam angle and the beam field relative to each other and relative to the illumination target.

When asymmetric illumination source 44 includes at least one row 50 of LED sets 52 that emit UV wavelengths, the control over spread angle and tunable cut-off provided by asymmetric illumination source 44 allows for precise control over the application of UV light in a location. For example, depending on which LED sets 52 are configured to emit UV wavelengths, one or more asymmetric illumination sources 44 positioned in a location can be driven to output UV wavelength solely in a direction that is above any participants or viewers, thereby providing upper air sterilization without harming attendees. Alternatively, asymmetric illumination sources 44 may have LED sets 52 that are configured to emit UV wavelengths onto all surfaces within the location that are within the entire field of illumination, or to concentrate UV illumination within particular beam angles and with specific cut-offs. As a result, a location outfitted with a series of asymmetric illumination sources 44 having LED sets 52 configured to emit UV wavelengths can be subjected to UV germicidal irradiation in a controlled and specific manner to ensure that sufficient UV illumination is provided for germicidal benefits and that all areas in the location receive sufficient UV illumination. For example, symmetric illumination sources 44 having LED sets 52 configured to emit UV wavelengths that are positioned on opposing sides of a location, such as sports field, can be driven in combination to eliminate shadowed areas and thus ensure that all surfaces within a location are adequately disinfected or sterilized as desired. The present invention may be used to perform a deep cleaning when a facility is empty of people using a focused UV beam on a particular section. When using a focused beam, there will be shadows created by seating and other structure. The present invention can then widen the UV beams for the widest possible coverage and run a supplemental disinfection routine with the wider UV beams reflecting off of more surfaces to provide more coverage on the previously shadowed areas. It should be recognized that a location could be outfitted with asymmetric illumination sources 44 that can produce both visible light and UV illumination, with asymmetric illumination sources 44 dedicated to providing UV illumination, and combinations thereof. Thus, some asymmetric illumination sources 44 may be used only when germicidal benefits are desired, or to enhance germicidal activities when a location is vacant to avoid any risk of inadvertent injuries.

Figure 24:
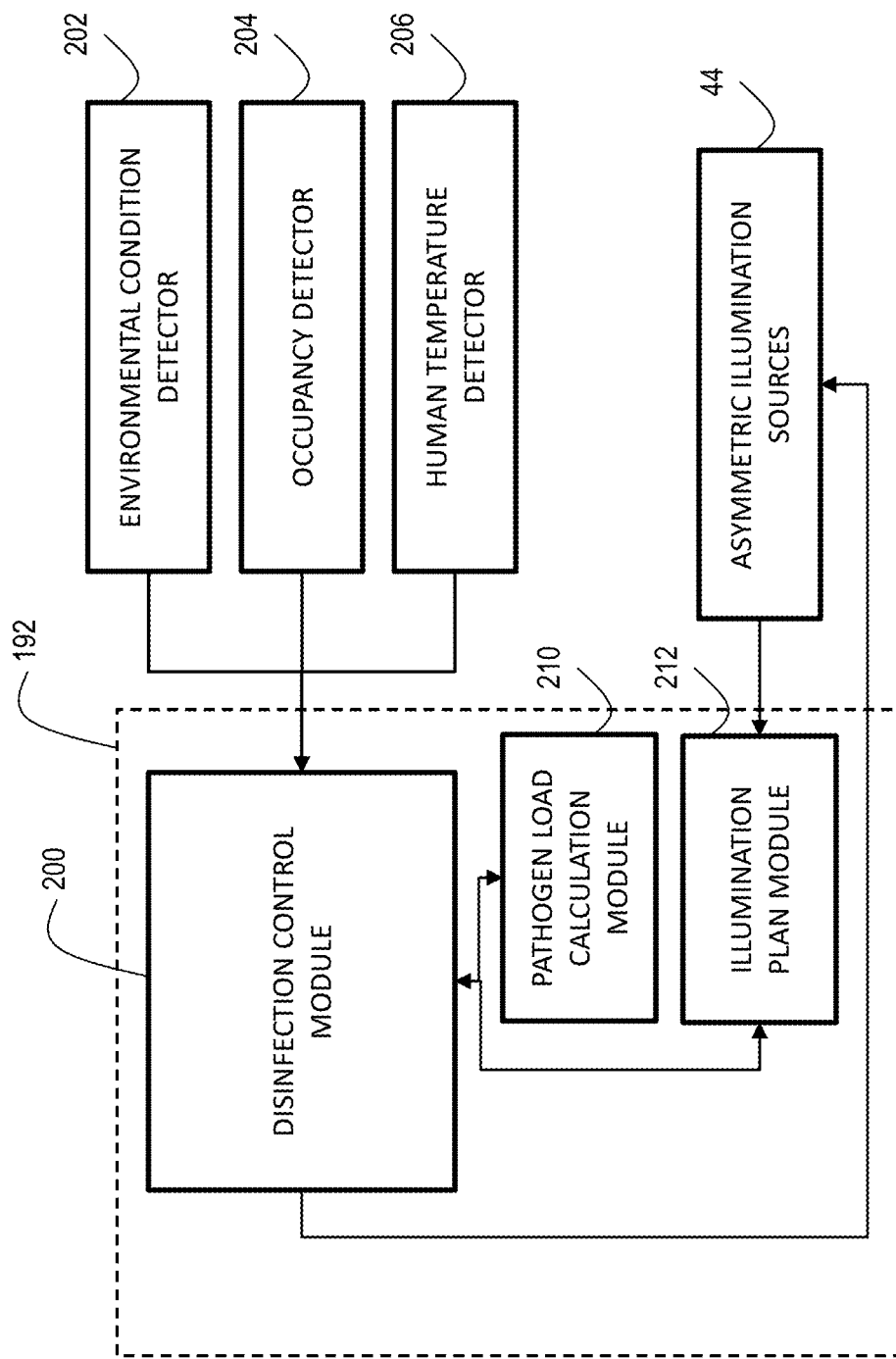
FIG. 24 is a flowchart of a disinfection control method for providing disinfecting using illumination sources with ultraviolet wavelength capabilities according to the present invention.

Referring to FIG. 24, system 10 may include a disinfection control module 200 for disinfecting location 14 based on the usage of location 14 and the disinfection capabilities of the specific asymmetric illumination sources 44 of location 14. Disinfection control module 200 is shown as implemented in remote host 192, but could be implemented at least partially in master enclosure controller 140, in dedicated hardware connected to an expansion header 152, or combinations thereof. Control module 200 is interconnected to sensors that provide information about the usage of location 14 and the potential pathogen load created by that usage. For example, disinfection control module 200 may be interconnected to environmental detectors 202 that reports on environmental conditions experienced at location 14 that relevant to pathogens, such a temperature and humidity. Control module 200 may also be interconnected to occupancy detectors 204 that can provide information about the human usage of location 14. Control module 200 may further be interconnected to human temperature detectors 206, such as infrared sensors, that can identify potential usage of location 14 by persons who may be infected with a contagious disease. Control module 200 is further programmed to include a pathogen load calculation module 210 that can calculate a probable pathogen load from the information provided by detectors 202, 204 and 206. Preferably, detectors 202, 204 and 206 are duplicated and distributed throughout location 14 so that the information collected by detectors 202, 204 and 206 can be assigned to predetermined sub-regions within location 14, as further described below. It should be recognized that other detectors could be interconnected to disinfection control module 200 to provide information relevant to potential pathogens, including rapid detection equipment that can provide an identification of the specific pathogens present in a location.

Disinfection control module 200 is associated with an illumination plan module 212 that can access data about asymmetric illumination sources 44 of location 14, including the position, orientation, and UV output of each asymmetric illumination source 44. Using the pathogen load determined by pathogen load calculation module 210 and specific data about each asymmetric illumination source 44, illumination plan module 212 determines how each asymmetric illumination source 44 should be driven to accomplish disinfection of location 14. Disinfection control module 200 may then command or drive asymmetric illumination sources 44 according to the illumination plan developed by illumination plan module 212. When disinfection control module 200 is implemented in remote host 192, each master enclosure controller 148 must be configured to response to command from remote host 192 then to drive each associated core enclosure 132 according to the illumination plan.

For example, processor 148 of master controller 140 may be programmed via an external user interface or software that resides on the cloud to run disinfection routines. Similar to the routines used for programming and operating entertainment lighting scenes, the user of system 10 can be provided with user inputs that are translated into system commands to build a specific disinfection scene. User inputs may include duration (time), nadir location (center point of light beam), beam angle X, beam angle y, sliders for intensity from various components of light spectrum, peak wavelength, etc. These pre-programmed scenes may be scheduled in advance to run at specific times within the day, week, month, etc, and may be made recurring events. These scenes may also be triggered manually to override previous scenes. If a particular scene contains any spectral wavelengths that the facility owner deems inappropriate for humans, occupancy sensors may override any programmed disinfecting scenes and return to a failsafe setting with safe light being provided.

Figure 25:
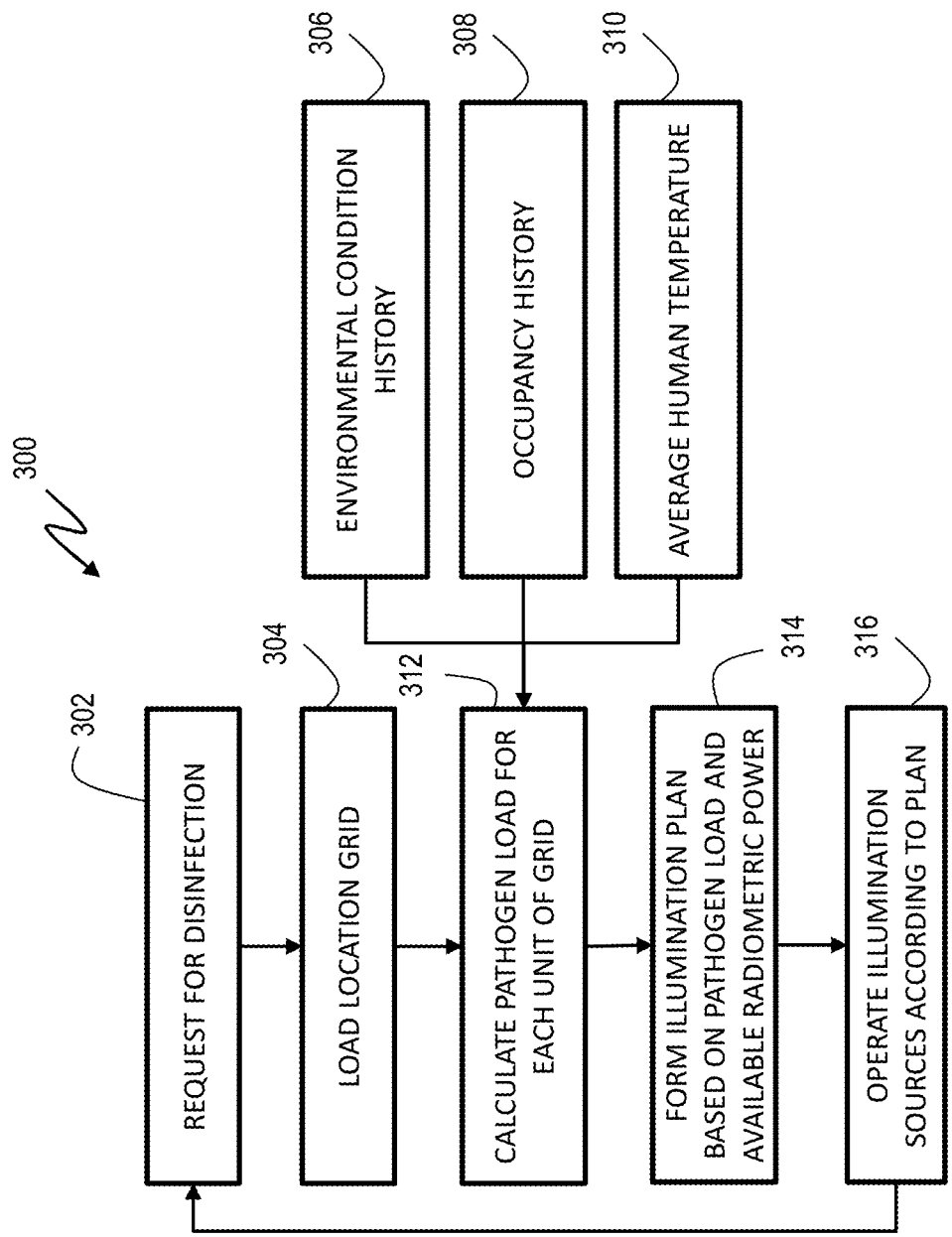
FIG. 25 is a flowchart of a safety method according to the present invention.

Referring to FIG. 25, the present invention includes a method 300 of disinfecting using asymmetric illumination sources 44 of location 14 that can be installed as software in core enclosure 132 and triggered from remote host 192, or run remotely from remote host 192, or combinations thereof. First, a request for disinfection is received 302. For example, remote host 192 can signal system 10 via wireless gateway 190 in response to a user input or according to a preprogrammed disinfecting schedule. Next, location 14 to be treated is partitioned or subdivided using a grid 304 into individual units or a comparable scheme for tracking sections of location 14. It should be recognized that grid 304 could be established on installation as a configuration or loaded on an ad hoc basic so that grid 304 could be easily adapted over time in responses to changes at location 14 or to improve operation of system 10 over time. Grid 304 includes an identification of or mapping to the particular asymmetric illumination sources 44 whose illumination will reach each unit of grid 304 and may include additional information such as the angle of illumination of each asymmetric illumination source 44 and the range of radiometric power that can be provided by each asymmetric illumination source 44. Method 300 then detects one or more of the environmental condition history 306 since the last disinfection, occupancy history 308 since the last disinfection, and average human temperature 310 since the last disinfection. These inputs are used to calculate the pathogen load 312 for each space of grid from step 304. The pathogen load may then be used to form an illumination plan 314 that takes into consideration the pathogen load and the available radiometric power to provide adequate disinfection. Each asymmetric illumination source 44 may then be operated 316 according to the illumination plan of step 314 to disinfect location 14. Method 300 thus provides for location-specific disinfection that can adjust in real-time according to the usage of location 14. As a result, method 300 avoids over-treatment, thereby saving energy by minimizing the amount of illumination to just the amount needed for disinfection. Method 300 thus also can reduce the amount of time spent disinfecting as lower usage of location 14 can result in shorter treatment times.

An example illumination plan is seen below in Table 1:

TABLE 1

Illumination Plan

| Grid Unit | Pathogen Load | Available Power (total UV intensity) | Illumination Plan |
|---|---|---|---|
| 1 | High | 8.75 µW/cm$^2$ | Illuminate associated sources for 12 minutes 15 seconds |
| 2 | High | 2.37 µW/cm$^2$ | Illuminate associated sources for 45 minutes 17 seconds |
| 3 | Medium | 8.75 µW/cm$^2$ | Illuminate associated sources for 8 minutes |
| 4 | Low | 2.37 µW/cm$^2$ | Illuminate associated sources for 20 minutes |
| 5 | Low | 8.75 µW/cm$^2$ | Illuminate associated sources for 4 minutes |
| 6 | Medium | 2.37 µW/cm$^2$ | Illuminate associated sources for 30 minutes |
| n | Medium | XXX mW/cm$^2$ | Illuminate associated sources for (mmm) minutes |

The formation of the illumination plan in step 314 can be designed to account for and balance factors such as the costs associated with energy demands of the illumination plan and the next time that location 14 will be occupied. For example, a location that does not need to be used for 24 hours can be treated more efficiently by disinfecting at a lower power over a longer time period than a location that needs to be disinfected quickly for an event a few hours later. Method 300 also allows for a location to be treated more efficiently by reducing energy used to treat unused location. For example, a stadium that only has one section of seats in use for an event will not result in stadium wide disinfection as the illumination with UV light can be restricted to just the portions of the stadium that were in use.

Figure 26:
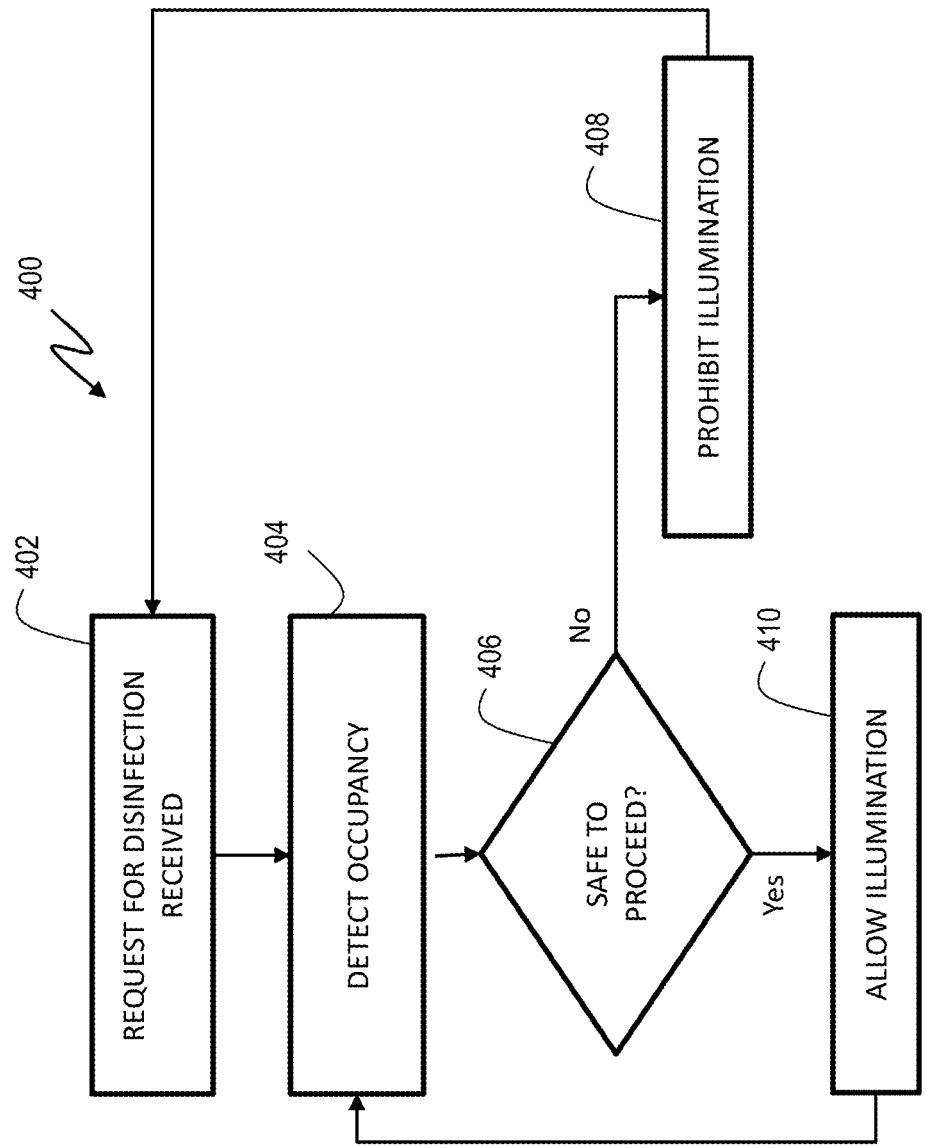

Referring to FIG. 26, a safety check method 400 may be used to prevent operation of system 10 according to the illumination plan. For example, receipt of a request for disinfection 402 may trigger occupancy sensors to detect for current occupancy 404. If a check 406 of the data from occupancy sensors indicates that people are present, and thus it is not safe to proceed, safety check method 400 can prohibit the illumination of any asymmetric illumination source 44 scheduled to provide UV illumination. If check 406 determines that it is safe to proceed because occupancy is negative, then safety check method 400 can allow illumination of any asymmetric illumination source 44 scheduled to provide UV illumination. Safety check method 400 can be implemented globally via remote host 192, or in specific locations on a master enclosure 140 by master enclosure 140 basis for added safety or for locations 14 with discrete areas that can be selectively disinfected despite occupancy in other locations. For example, it may be possible to disinfect the stands of a stadium safely despite players training on the field.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A lighting system, comprising:
a luminaire having a housing extending along a longitudinal axis and having an elongated opening;
an illumination source positioned in the elongated opening of the housing of the luminaire, having at least two independently controllable rows of light emitting diodes that extend along the longitudinal axis, and one of the independently controllable rows of light emitting diodes comprises light emitting diodes that emit illumination having wavelengths in the ultraviolet spectrum; and
a controller, interconnected to the illumination source that is programmed to control when the light emitting diodes that emit illumination having wavelengths in the ultraviolet spectrum are illuminated, comprising:
- a first detector, interconnected to the controller, that provides data regarding environmental conditions proximate to the illumination source;
- a second detector, interconnected to the controller, that provides data regarding occupancy of a location proximate to the illumination source; and
- a pathogen load calculator that can determine a pathogen load for at least a portion of the location proximate to the illumination source;
- wherein, the light emitting diodes that emit illumination having wavelengths in the ultraviolet spectrum emits light with wavelengths between 100 to 290 nanometers; and
- wherein, the light emitting diodes that emit illumination having wavelengths in the ultraviolet spectrum emits light having a peak wavelength between 250 to 280 nanometers.

2. The lighting system of claim 1, wherein the controller includes an illumination planner that can determine an illumination plan describing how the illumination source must be driven to provide sufficient illumination to disinfect the portion of the location proximate to the illumination source according to the pathogen load.

3. The lighting system of claim 2, wherein the controller is programmed to cause illumination of the illumination source according to the determination by the illumination planner of how the illumination source must be driven to provide sufficient illumination to disinfect the portion of the location proximate to the illumination source.

4. The lighting system of claim 3, further comprises a plurality of luminaires, each of which includes an illumination source having at least one independently controllable row of light emitting diodes that emits illumination having wavelengths in the ultraviolet spectrum.

5. The lighting system of claim 4, wherein the illumination planner of the controller is programmed to determine a plurality of illumination plans, each of which corresponds to one of the plurality of luminaires.

6. The lighting system of claim 5, wherein the controller is positioned in a remote host that is in wireless communication with each of the plurality of luminaires.

* * * * *